United States Patent

Stern et al.

[11] Patent Number: 6,075,883
[45] Date of Patent: Jun. 13, 2000

[54] METHOD AND SYSTEM FOR IMAGING AN OBJECT OR PATTERN

[75] Inventors: Howard Stern, Greenlawn; Fereydoun Maali, New York, both of N.Y.

[73] Assignee: Robotic Vision Systems, Inc., Hauppauge, N.Y.

[21] Appl. No.: 08/748,040

[22] Filed: Nov. 12, 1996

[51] Int. Cl.[7] .................................................. G06K 9/00
[52] U.S. Cl. ........................................ 382/144; 382/149
[58] Field of Search .................................... 382/144, 145, 382/146, 147, 149, 150, 151; 352/376, 237; 348/87, 125, 126

[56] References Cited

U.S. PATENT DOCUMENTS

| | | |
|---|---|---|
| 891,013 | 6/1908 | Smith . |
| 1,596,458 | 8/1926 | Schiesari . |
| 2,177,737 | 10/1939 | Mohr et al. . |
| 3,479,945 | 11/1969 | Koch . |
| 4,146,327 | 3/1979 | Harris . |
| 4,152,723 | 5/1979 | McMahon et al. . |
| 4,238,147 | 12/1980 | Stern . |
| 4,286,293 | 8/1981 | Jablonowski . |
| 4,343,553 | 8/1982 | Nakagawa et al. . |
| 4,441,124 | 4/1984 | Heebner et al. . |
| 4,443,705 | 4/1984 | DiMatteo et al. . |
| 4,494,874 | 1/1985 | DiMatteo et al. . |
| 4,527,893 | 7/1985 | Taylor . |
| 4,529,316 | 7/1985 | DiMatteo . |
| 4,590,367 | 5/1986 | Ross et al. . |
| 4,594,001 | 6/1986 | DiMatteo et al. . |
| 4,645,348 | 2/1987 | Dewar et al. . |
| 4,682,894 | 7/1987 | Schmidt et al. . |
| 4,688,939 | 8/1987 | Ray . |
| 4,740,708 | 4/1988 | Batchelder . |
| 4,762,990 | 8/1988 | Caswell et al. . |
| 4,824,251 | 4/1989 | Slotwinski et al. . |
| 4,925,308 | 5/1990 | Stern et al. . |
| 4,957,369 | 9/1990 | Antonsson . |
| 4,976,356 | 12/1990 | Mizuno et al. . |
| 4,982,103 | 1/1991 | Meiffren et al. . |

(List continued on next page.)

FOREIGN PATENT DOCUMENTS 62-79644  4/1987  Japan .
63-5243   1/1988  Japan .

OTHER PUBLICATIONS

View 830 Brochure, 5 pgs., View Engineering, Inc., 1993.
View 830 Brochure, 4 pgs., View Engineering, Inc. Feb. 1995.

(List continued on next page.)

*Primary Examiner*—Joseph Mancuso
*Attorney, Agent, or Firm*—Kenyon & Kenyon

[57] ABSTRACT

A system for simultaneously obtaining a plurality of images of an object or pattern from a plurality of different viewpoints is provided. Proper image contrast is obtained by replacing the light sources of earlier systems with equivalent light sensitive devices and replacing the cameras of earlier systems with equivalent light sources. Bright-field and dark-field images may be simultaneously obtained. In another aspect, a light source is positioned to illuminate at least some of an object. A plurality of light guides are positioned to simultaneously receive light reflected from the object and transmit it to a plurality of photodetectors. The light guides are arranged so their respective input ends are spaced substantially equally along at least a portion of a surface of an imaginary hemisphere surrounding the object. The signals from the photodetectors are processed and a plurality of images are formed. Another aspect provides generating composite images from simultaneously obtained images. Equivalent regions of each image geographically identical subpictures) are compared. The subpicture having the highest entropy is selected and stored. This process continues for all subpictures. A new composite picture is generated by combining the selected subpictures. In another aspect, the vector of relative light values gathered for each pixel or region of an object illuminated or scanned is used to determine reflectance properties of points or regions illuminated on the object or pattern. The reflectance properties may be stored in a matrix and the matrix used to read, for example, a Bar Code of a data matrix symbol.

22 Claims, 16 Drawing Sheets

U.S. PATENT DOCUMENTS

| | | |
|---|---|---|
| 4,991,968 | 2/1991 | Yonescu et al. . |
| 5,030,008 | 7/1991 | Scott et al. . |
| 5,060,065 | 10/1991 | Wasserman . |
| 5,091,692 | 2/1992 | Ohno et al. . |
| 5,172,005 | 12/1992 | Cochran et al. . |
| 5,179,413 | 1/1993 | Griffith . |
| 5,208,463 | 5/1993 | Honma et al. . |
| 5,230,027 | 7/1993 | Kikuchi . |
| 5,245,421 | 9/1993 | Robertson et al. . |
| 5,247,585 | 9/1993 | Watanabe . |
| 5,260,779 | 11/1993 | Wasserman . |
| 5,305,091 | 4/1994 | Gelbart et al. . |
| 5,347,363 | 9/1994 | Yamanaka . |
| 5,351,126 | 9/1994 | Takada et al. . |
| 5,365,084 | 11/1994 | Cochran et al. . |
| 5,365,341 | 11/1994 | Sugawara . |
| 5,367,439 | 11/1994 | Mayer et al. . |
| 5,371,375 | 12/1994 | Stern et al. . |
| 5,384,000 | 1/1995 | Nishiguchi . |
| 5,399,870 | 3/1995 | Torii et al. . |
| 5,406,372 | 4/1995 | Vodanovic et al. . |
| 5,448,650 | 9/1995 | Desai et al. . |
| 5,455,870 | 10/1995 | Sepai et al. . |
| 5,461,417 | 10/1995 | White et al. . |
| 5,463,213 | 10/1995 | Honda . |
| 5,463,227 | 10/1995 | Stern et al. . |
| 5,465,152 | 11/1995 | Bilodeau et al. . |
| 5,490,084 | 2/1996 | Okubo et al. . |
| 5,506,793 | 4/1996 | Straayer et al. . |
| 5,509,104 | 4/1996 | Lee et al. . |
| 5,510,625 | 4/1996 | Pryor et al. . |
| 5,517,235 | 5/1996 | Wasserman . |
| 5,528,371 | 6/1996 | Sato et al. . |
| 5,546,189 | 8/1996 | Svetkoff et al. . |
| 5,550,583 | 8/1996 | Amir et al. . |
| 5,635,697 | 6/1997 | Shellhammer et al. . |
| 5,635,700 | 6/1997 | Fazekas . |

OTHER PUBLICATIONS

View 880 Brochure, 6 pgs., View Engineering, Semiconductor Products Group, Simi Walley, CA.

View 880 Brochure, 2 pgs., View Engineering, Semiconductor Products Group, Simi Valley, CA., Dec. 1994.

View PR–2000, 2 pgs., View Engineering, Inc., 1995.

WF–703DUO™ In–Line Wafer Inspection System, 2 pgs., Semiconductor International, Jan. 1997.

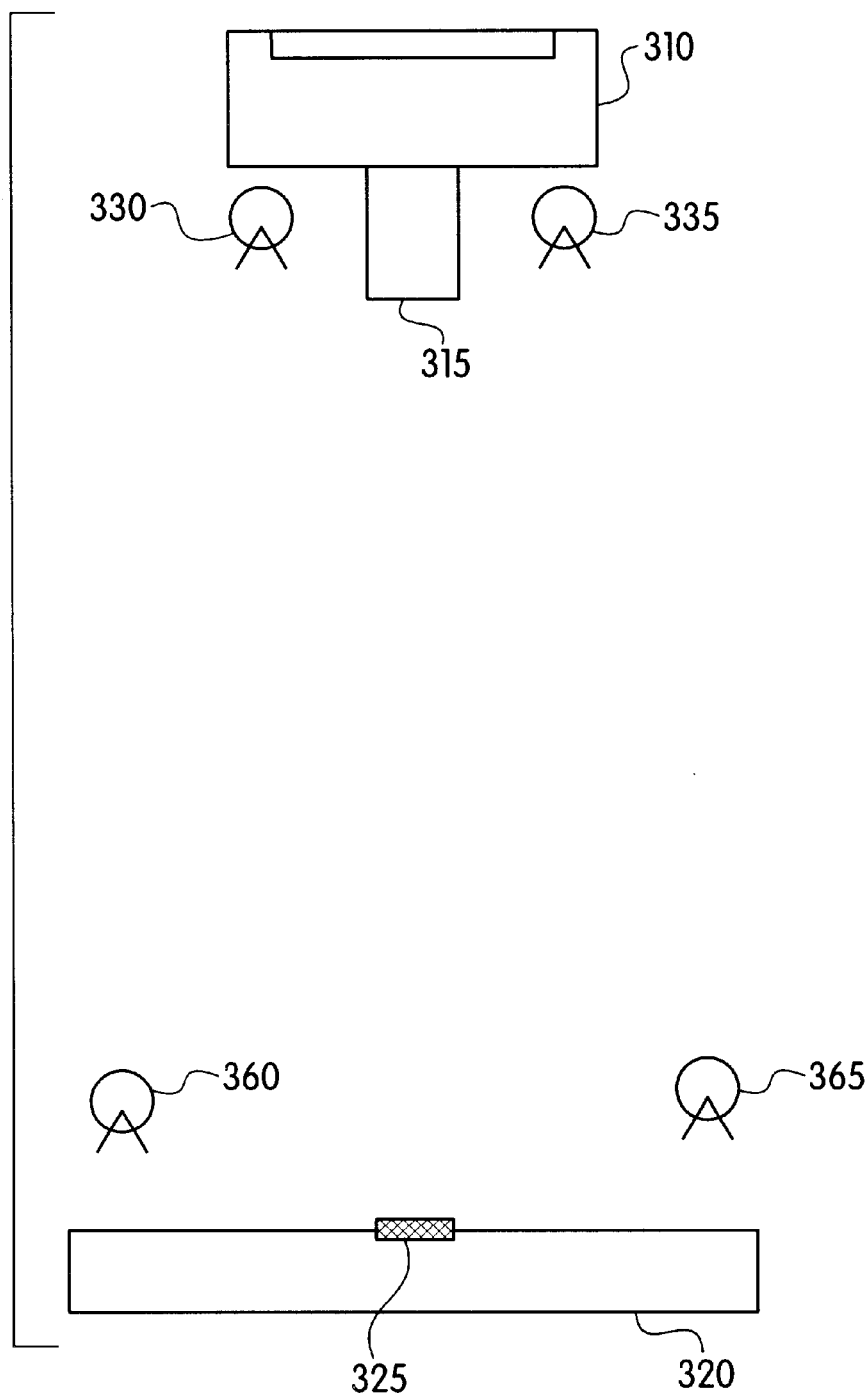

| 1 | 1 | 1 | 1 | 1 | 0 | 0 | 0 | 1 | 1 | 1 | 1 | 0 | 0 | 0 | 1 | 1 | 0 | 0 | 0 |
|---|---|---|---|---|---|---|---|---|---|---|---|---|---|---|---|---|---|---|---|
| 1 | 1 | 1 | 1 | 1 | 0 | 0 | 0 | 1 | 1 | 1 | 1 | 0 | 0 | 0 | 1 | 1 | 0 | 0 | 0 |
| 1 | 1 | 1 | 1 | 1 | 0 | 0 | 0 | 1 | 1 | 1 | 1 | 0 | 0 | 0 | 1 | 1 | 0 | 0 | 0 |
| 0 | 0 | 0 | 1 | 1 | 0 | 0 | 0 | 1 | 1 | 1 | 1 | 0 | 0 | 0 | 1 | 1 | 1 | 1 | 0 |
| 0 | 0 | 0 | 1 | 1 | 0 | 0 | 0 | 0 | 0 | 0 | 0 | 0 | 0 | 0 | 1 | 1 | 1 | 1 | 0 |
| 0 | 0 | 0 | 1 | 1 | 0 | 0 | 0 | 0 | 0 | 0 | 0 | 0 | 0 | 0 | 0 | 0 | 0 | 0 | 0 |
| 0 | 0 | 0 | 0 | 0 | 0 | 0 | 0 | 1 | 1 | 1 | 1 | 1 | 1 | 1 | 0 | 0 | 0 | 0 | 0 |
| 0 | 0 | 0 | 0 | 0 | 0 | 0 | 0 | 1 | 1 | 1 | 1 | 0 | 0 | 0 | 0 | 0 | 0 | 0 | 0 |
| 0 | 0 | 1 | 1 | 1 | 0 | 0 | 0 | 1 | 1 | 1 | 1 | 0 | 0 | 0 | 0 | 0 | 0 | 1 | 1 |
| 0 | 0 | 1 | 1 | 1 | 1 | 0 | 0 | 0 | 0 | 0 | 0 | 0 | 0 | 0 | 0 | 0 | 0 | 0 | 0 |
| 0 | 0 | 1 | 1 | 1 | 1 | 0 | 0 | 1 | 1 | 1 | 1 | 1 | 1 | 0 | 0 | 0 | 0 | 0 | 0 |
| 0 | 0 | 0 | 0 | 0 | 0 | 0 | 0 | 1 | 1 | 1 | 1 | 1 | 1 | 0 | 0 | 0 | 0 | 0 | 0 |
| 0 | 0 | 0 | 0 | 0 | 0 | 0 | 0 | 1 | 1 | 1 | 1 | 1 | 1 | 1 | 1 | 1 | 1 | 1 | 0 |
| 0 | 0 | 0 | 0 | 0 | 0 | 0 | 0 | 0 | 0 | 0 | 0 | 0 | 0 | 0 | 0 | 0 | 1 | 1 | 1 |
| 1 | 1 | 1 | 1 | 1 | 1 | 0 | 0 | 0 | 0 | 0 | 0 | 0 | 0 | 0 | 0 | 0 | 1 | 1 | 1 |
| 1 | 1 | 1 | 1 | 1 | 1 | 0 | 0 | 0 | 0 | 0 | 0 | 0 | 0 | 0 | 0 | 0 | 1 | 1 | 1 |
| 1 | 1 | 1 | 1 | 1 | 1 | 0 | 0 | 0 | 0 | 0 | 0 | 0 | 0 | 1 | 1 | 1 | 1 | 1 | 1 |
| 0 | 0 | 0 | 0 | 1 | 1 | 0 | 0 | 1 | 1 | 1 | 0 | 0 | 0 | 1 | 1 | 1 | 1 | 1 | 1 |
| 0 | 0 | 0 | 0 | 1 | 1 | 0 | 0 | 1 | 1 | 1 | 0 | 0 | 0 | 0 | 0 | 0 | 0 | 0 | 0 |
| 0 | 0 | 0 | 0 | 1 | 1 | 0 | 0 | 1 | 1 | 1 | 0 | 0 | 0 | 0 | 0 | 0 | 0 | 0 | 0 |

FIG. 9

METHOD AND SYSTEM FOR IMAGING AN OBJECT OR PATTERN

FIELD OF INVENTION

The present invention is directed to a system and method for imaging objects or patterns. More particularly, the present invention is directed to a system and method for simultaneously obtaining a plurality of images of an object or pattern from a plurality of different viewpoints.

COPYRIGHT NOTICE

A portion of the disclosure of this patent document contains material which is subject to copyright protection. The copyright owner has no objection to the facsimile reproduction by anyone of the patent document or patent disclosure as it appears in the Patent and Trademark Office, patent file or records, but otherwise reserves all copyright rights whatsoever.

BACKGROUND OF THE INVENTION

Machine vision systems are commonly used in industry for high speed inspections. In particular, these systems are used to obtain digital images of objects in order to determine, with a computer, whether the object is of "acceptable" quality with respect to predetermined specifications. For example, a system may inspect a semiconductor chip package to determine whether each of the leads of the package have the proper dimensions. A system may also inspect for coplanarity of solder balls on ball grid arrays.

Patterns such as bar codes and data codes are also imaged by such systems. Images of these patterns are analyzed by a computer and in order to "read" the information represented by these codes.

In a machine vision system, an object (or pattern) is typically imaged by illuminating the object with light sources and capturing the light reflected from the object with a video camera (i.e., a photodetector). A digital image is formed from the image received by the camera and the digital data is analyzed by a computer in order to determine characteristics of the object or pattern.

Obtaining a proper contrast between the object or pattern and the background is critical to obtaining an image of sufficient clarity for accurate analysis by a computer. In current practice, an engineer or knowledgeable user obtains the proper contrast by varying the positions of the light sources with respect to the object or pattern being viewed and with respect to the video camera recording the scene. Additionally, the intensity and possibly the polarization and color of the light sources are varied. To achieve the desired contrast, the illumination is often manipulated to make the background either dark with respect to the object features or pattern (dark-field illumination) or bright with respect to the object features or pattern (bright-field illumination). Obtaining the proper illumination is particularly difficult when working with specular (mirror-like) surfaces, especially when the specular surfaces are curved or multifaceted.

One technique for illuminating an object for imaging purposes is described in U.S. Pat. No. 5,461,417 issued to White et al. (the "White '417" patent), expressly incorporated herein by reference. The White '417 patent discloses a system for providing a continuous, uniform, diffuse lighting environment. This system is satisfactory for certain types of applications. Another technique for illumination is described in U.S. Pat. No. 5,187,611 issued to White et al., expressly incorporated herein by reference. In this patent, a Diffuse On-Axis Light (DOAL) is described which is also beneficial in certain applications. However, good contrast sometimes requires edges to be highlighted which is best obtained from collimated unidirectional light, not uniformly diffuse light.

For certain objects, it may be advantageous to sequentially illuminate an object from a number of different viewpoints and take a picture of the object for each illumination. The pictures can then be combined into a single image. Such a system is described in U.S. Pat. No. 5,060,065 issued to Wasserman, expressly incorporated herein by reference. It may be desirable, for example, to image an object using a bright-field illumination method and subsequently image the same object using a dark-field illumination method. The bright-field and dark-field images can then be individually analyzed or can be first combined, and then analyzed.

Unfortunately, the sequential illumination method increases capture time since a separate picture is required for each illumination—each video picture typically requires $\frac{1}{30}$ second. Thus, if lights at three different locations from the object are utilized, three pictures would be required.

Furthermore, the combined image tends to look smeared if there is any relative motion between the object and the camera. For example, vibration may cause the object to move slightly. Since an image of the object before the motion and after the motion will not exactly coincide, the combined image will appear smeared.

SUMMARY OF THE INVENTION

The present invention provides a system and method for simultaneously obtaining a plurality of images of an object or pattern from a plurality of different viewpoints. In an exemplary embodiment of the invention, proper image contrast is obtained by replacing the light sources of earlier systems with equivalent light sensitive devices and replacing the cameras of earlier systems with equivalent light sources. With such a system, bright-field images and dark-field images may be simultaneously obtained.

In one aspect of the invention, a light source is positioned to illuminate at least a portion of an object. A plurality of light guides having input ends are positioned to simultaneously receive light reflected from the object and transmit the received light to a plurality of photodetectors. The light guides are arranged such that their respective input ends are spaced substantially equally along at least a portion of a surface of an imaginary hemisphere surrounding the object. The signals generated by the photodetectors (as a result of light detection) are processed and a plurality of images of the object are formed.

Another aspect of the invention provides a method for generating composite images from simultaneously obtained images. Equivalent regions of each image (corresponding to geographically identical subpictures) are compared. The subpicture having the highest entropy is selected and stored. This process continues until all subpictures have been considered. A new composite picture is generated by pasting together the selected subpictures.

In another aspect of the invention, the vector of relative light values gathered for each pixel or region of an object illuminated or scanned (i.e., one value for each photodetector) is used to determine reflectance properties of points or regions illuminated on the object or pattern. The reflectance properties may be stored in a matrix and the matrix used to read, for example, a Bar Code.

BRIEF DESCRIPTION OF THE DRAWINGS

The foregoing and other features of the present invention will be more readily apparent from the following detailed description of exemplary embodiments taken in conjunction with the attached drawings wherein:

FIG. 3 illustrates a sequential illumination system;

FIG. 9 illustrates a matrix representing reflectance properties of a 2-D Bar Code;

DETAILED DESCRIPTION

Figure 1A:
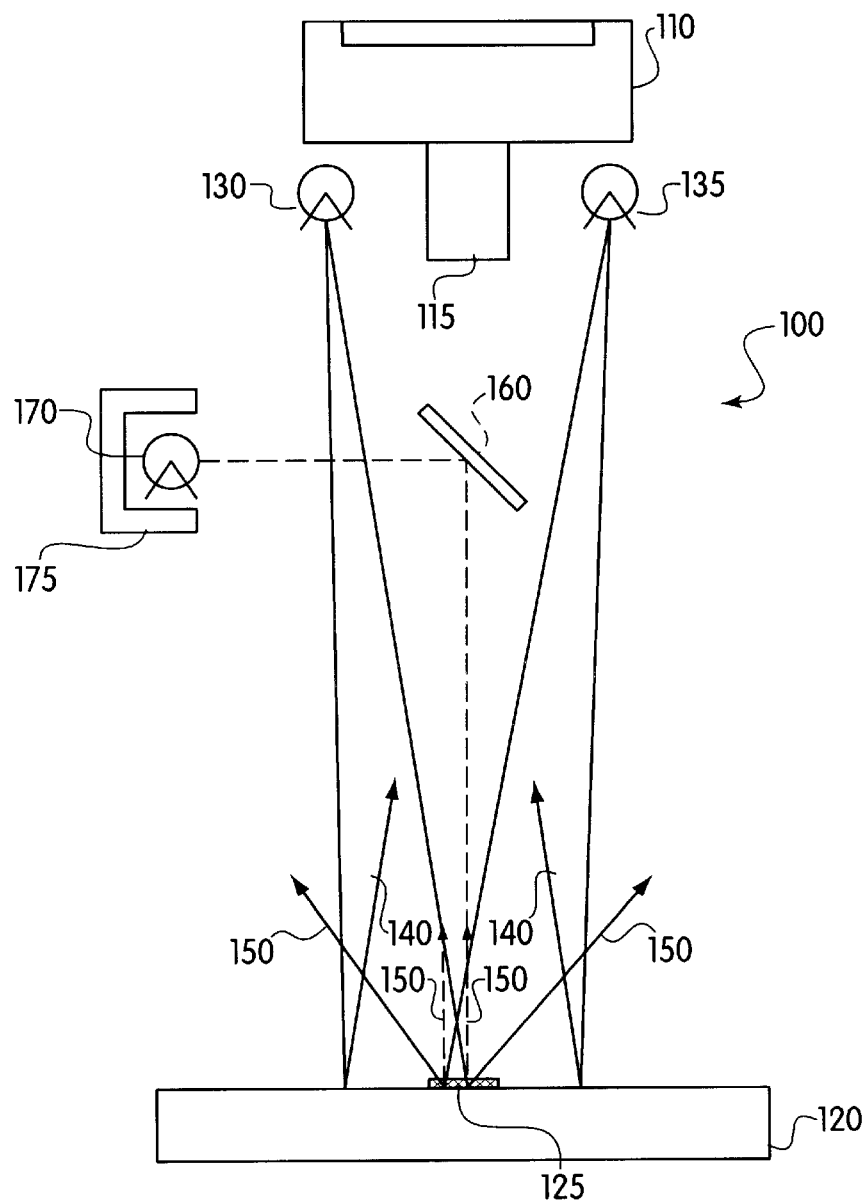
FIG. 1A is a diagram of a bright-field illumination system.
Figure 1B:
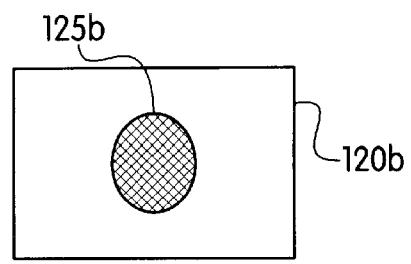
FIG. 1B is an illustration of an image obtained using the bright-field method of illumination.
Figure 10A:
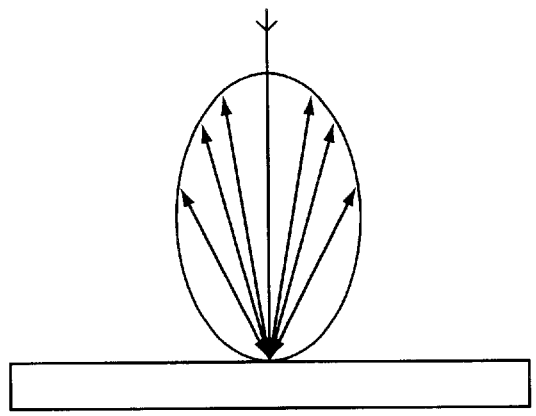
FIG. 10A illustrates reflecting properties of a shiny surface.
Figure 10B:
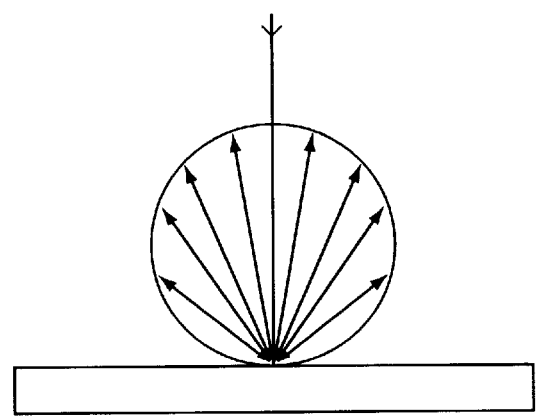
FIG. 10B illustrates reflecting properties of a diffuse surface.
Figure 10C:
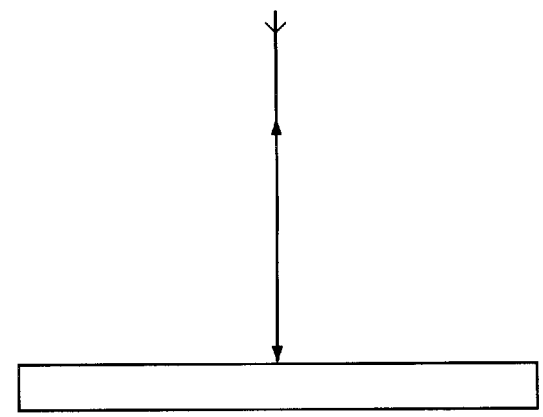
FIG. 10C illustrates reflecting properties of a mirror (specular) surface.

Bright-field Illumination: Referring now to the drawings, and initially FIG. 1A, there is illustrated a simple bright-field illumination system 100. A video camera 110 having a lens 115 is positioned to image a shiny plate 120 having a diffuse (Lambertian) gray circle 125 painted on it. The reflecting properties of shiny, diffuse, and mirror (specular) surfaces are shown in FIGS. 10A, 10B, and 10C respectively. The shiny plate 120 is orthogonal to the viewing axis of the camera 110. Two light sources ("upper light sources") 130 and 135, positioned equi-distantly from the shiny plate 120 and in close proximity to the camera lens 115, illuminate the shiny plate 120 and gray circle 125. The shiny plate 120 reflects light directly back to the camera 110. The circle 125, since it is diffuse, scatters the light 150. FIG. 1B illustrates the bright-field image formed by the camera 110. As shown, the image of the circle 125B appears dark relative to the bright background 120B. If the shiny plate is replaced with a true mirror, beam splitter 160 and lamp 170 would be required to direct the light parallel to the camera axis to obtain true bright-field illumination.

Figure 2A:
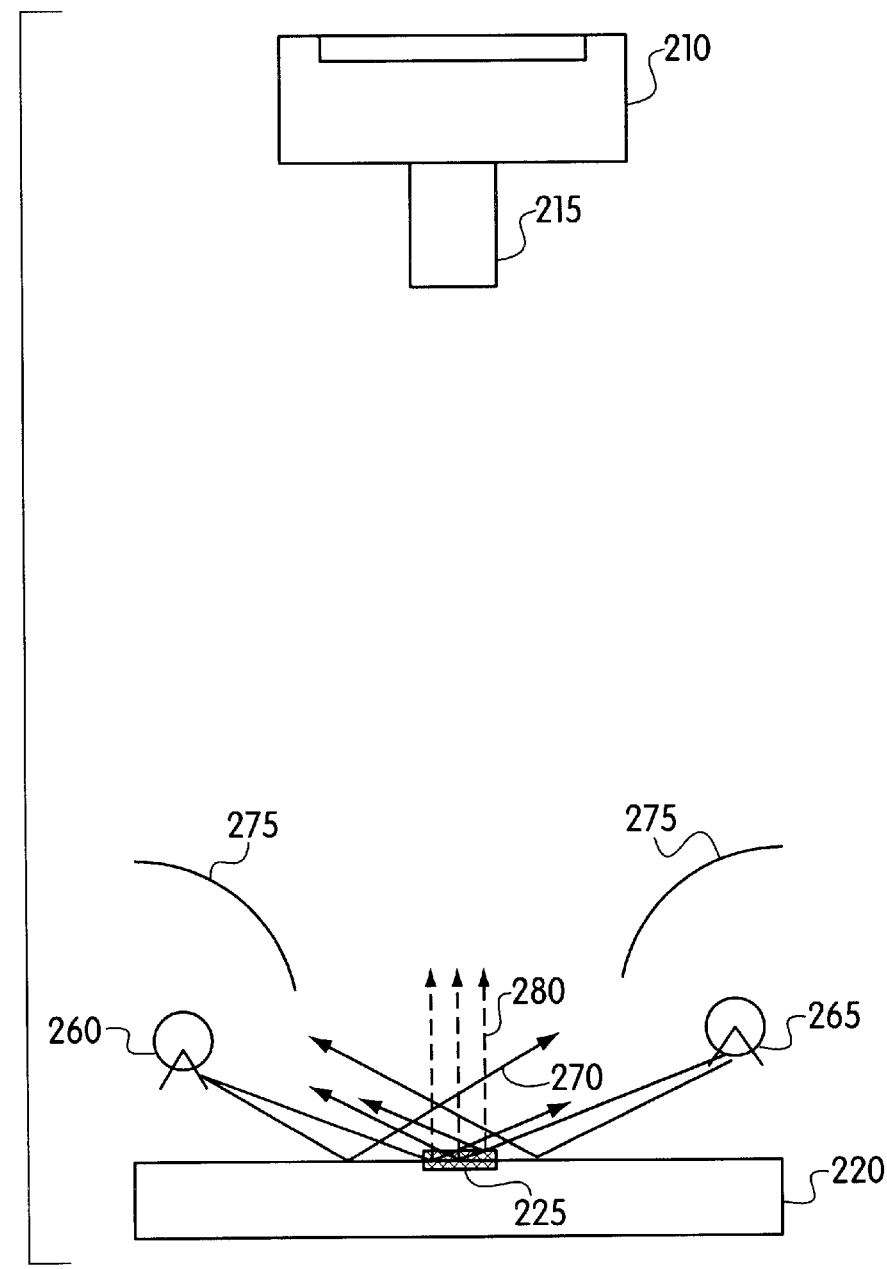
FIG. 2A is a diagram of a dark-field illumination system.
Figure 2B:
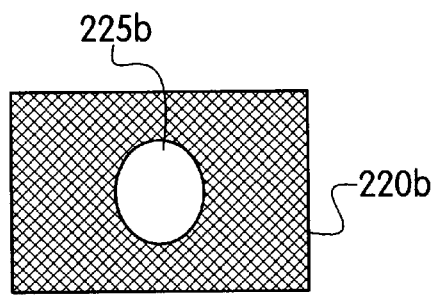
FIG. 2B is an illustration of an image obtained using the dark-field method of illumination.

Dark-field Illumination: FIG. 2A illustrates a dark-field illumination system. In this system, a camera 210, lens 215, and shiny plate 220 with a gray circle 225 are positioned in the same manner as in FIG. 1A. Here, however, light sources ("lower light sources") 260 and 265 are each positioned off to the side (with respect to the camera 210 field of view) and close to the shiny plate 220. The light sources 260 and 265 are also positioned approximately equi-distantly from the shiny plate 220. Light shrouds 275 prevent light from passing directly from lamps 260 and 265 to lens 215. Light emanating from the light sources 260 and 265 is reflected as light 270 by the shiny plate 220 in a direction away from the camera lens 215. Light impinging on the gray circle 225 is scattered. As illustrated, at least some light (280) of the light impinging on the gray circle 225 is reflected toward the camera lens 215. FIG. 2B illustrates the dark-field image captured by the camera 210. Here, the image of the circle 225B appears bright relative to the dark background 220B.

Combined System: In both the bright-field illumination system and the dark-field illumination system, if the shiny surface (in FIGS. 1A and 2A) is not perfectly flat, other bright and dark regions may appear in the image background. For example, the surface may reflect in such a way to create both real and virtual images, each of which is imaged by the video camera. Thus, it may be desirable to illuminate an object from two or more different angles (with respect to the object). Accordingly, as illustrated in FIG. 3, a single system may include upper light sources 330 and 335 (corresponding to light sources 130 and 135 of FIG. 1A) and lower light sources 360 and 365 (corresponding to light sources 260 and 265 of FIG. 2A). Each set of light sources (i.e., upper light sources 330 and 335, and lower light sources 360 and 365) may be independently used to illuminate the object (here, shiny plate 320 with gray circle 325), with an image being captured by the video camera 310 for each. The most "useful" portions of the bright-field image and the dark-field image captured can be analyzed independently or can be combined to provide a single image of the object.

Points on some surfaces have complex reflectance properties that are combinations of those shown in FIGS. 10A, 10B, and 10C. Also, there may be surface regions viewed by the system of FIG. 3 that are curved or tilted with respect to the horizontal, which may spoil the bright-field or dark-field views. Therefore, the system of FIG. 3 may not satisfy a wide range of conditions that include unusual reflectance characteristics, or curved, or multi-sloped surfaces.

As noted above, this sequential illumination method increases capture time since a picture, e.g., a video frame, is required for each illumination. Furthermore, the combined image will appear smeared if there is any relative movement between the camera and the object.

Exemplary Embodiment: The present invention solves many imaging problems by simultaneously obtaining a plurality of images of the object. Specifically, the present invention provides the proper "contrast" by replacing the light sources of earlier systems with equivalent "cameras" and the cameras of the earlier systems with equivalent light sources. With such a system, a wide choice of illumination viewpoints may be obtained to obtain bright-field or dark-field images regardless of the exact local surface properties or orientation of the object or pattern being viewed.

Figure 4A:
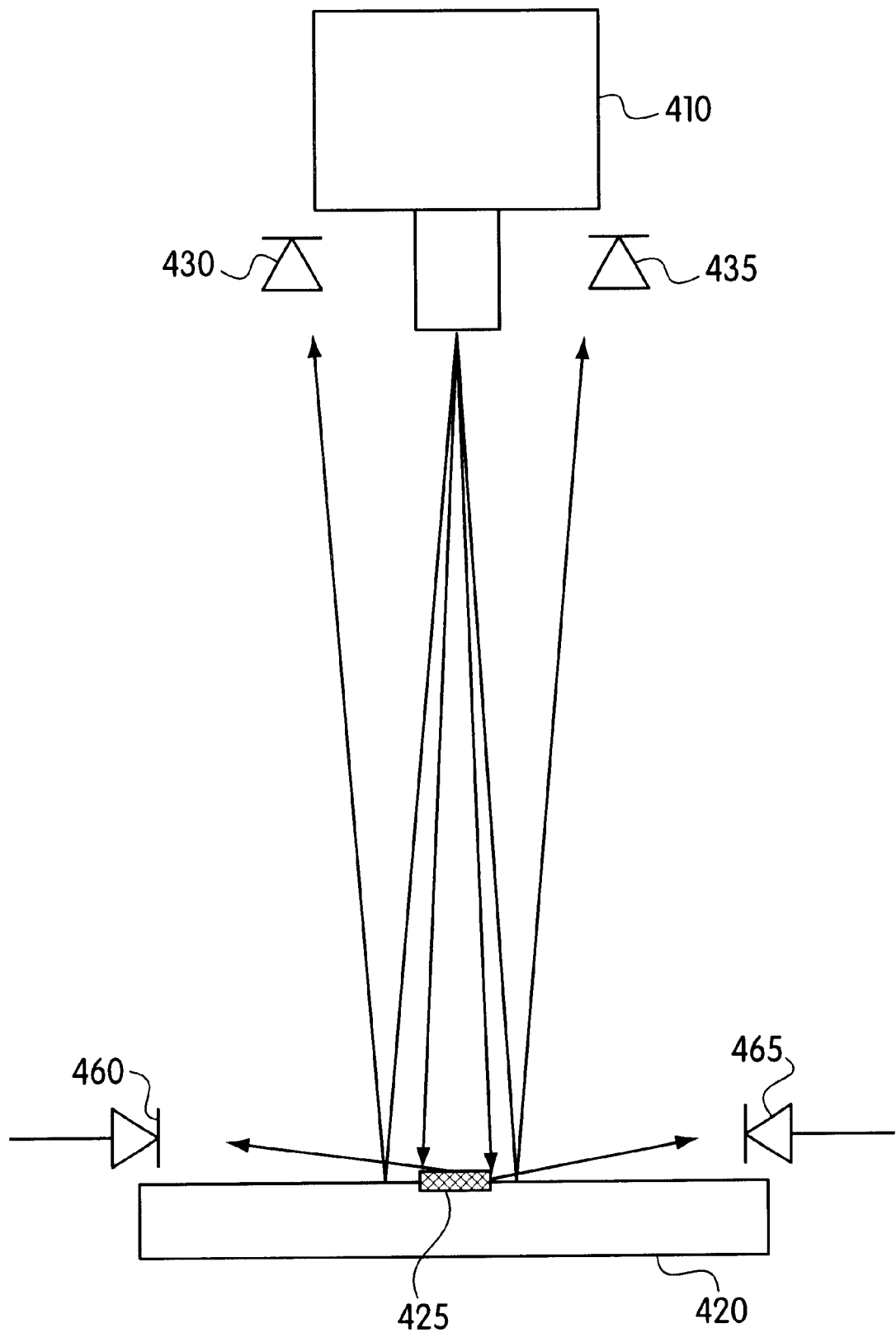
FIG. 4A is a diagram of an exemplary system illustrating the principles of the present invention.

An exemplary system implementing the principles of the present invention is illustrated in FIG. 4A. A scanner 410 is positioned to illuminate a shiny plate 420 having a diffuse gray circle 425 painted on it. The scanner 410, which has a light beam that may be, for example, continuous or AC or pulse modulated, generates a raster scanned light spot that scans across the object but emanates from the location previously occupied by the camera lens 315 of FIG. 3. The light spot may be "white" or a single color as is generated, for example, by a light emitting diode (LED). Alternatively, the light spot may be a single wavelength as may be generated by a laser.

As illustrated in FIG. 4A, the light sources of FIG. 3, i.e., 330, 335, 360, and 365, are replaced with photodetectors 430, 435, 460, and 465 such as, for example, photodiode pickups. Because the light spot is scanned in a raster pattern, each of the photodetectors 430, 435, 460, and 465 generates a "video" signal that is synchronized with all other photodetectors 430, 435, 460, and 465. That is, at each instant of time, the signal generated at each photodetector 430, 435, 460, and 465 is as a result of the illumination of the same "pixel" (light spot on a small region of the object). However, the signals generated at each photodetector 430, 435, 460, and 465 vary in amplitude according to the reflectance properties and orientation of the area being illuminated with respect to the relative position of the scanner 410 and the photodetector 430, 435, 460, and 465.

Due to the reversibility of light rays, a region of the object (i.e., the shiny plate 420) that would appear bright to the camera 310 of FIG. 3 when illuminated by a particular light source, will generate a strong signal when illuminated with a light source (i.e., scanner 410) at the position of the original camera, but sensed by a photodetector at the location of the original light source. Similarly, a region that appeared to be dim to the camera 310 of FIG. 3 when illuminated by a particular light source will generate a weak signal when illuminated with a light source (scanner 310) at the position of the original camera 310 of FIG. 3, but sensed by a light sensor at the location of the original light source. Thus, when the background of the shiny plate 420 is illuminated by the scanner 410, photodetectors 430 and 435 generate a relatively strong signal while photodetectors 460 and 465 generate a relatively weak signal. Furthermore, when the gray diffuse circle 425 is illuminated by the scanner 410, photodetectors 430 and 435 generate a relatively weak signal while photodetectors 460 and 465 generate relatively strong signals. Accordingly, photodetectors 430 and 435 capture bright-field images of the shiny plate 420 while photodetector 460 and 465 capture dark-field images of the shiny plate 420.

Applying the principles of the present invention, many equivalent "illumination viewpoints" can be simultaneously captured by strategically positioning simple light pickups such as, for example, photodiodes at viewpoints surrounding the object to be viewed. Accordingly, bright-field images and dark-field images from different viewpoints can simultaneously be captured.

In accordance with the principles of the present invention, the light sensitive devices of the illustrated embodiments may employ lenses, fiber optics, light guides, or simple photodetectors. The photodetectors may be photomultipliers or semiconductor photodiodes such as, for example, avalanche photodiodes, or phototransistors.

Figure 4B:
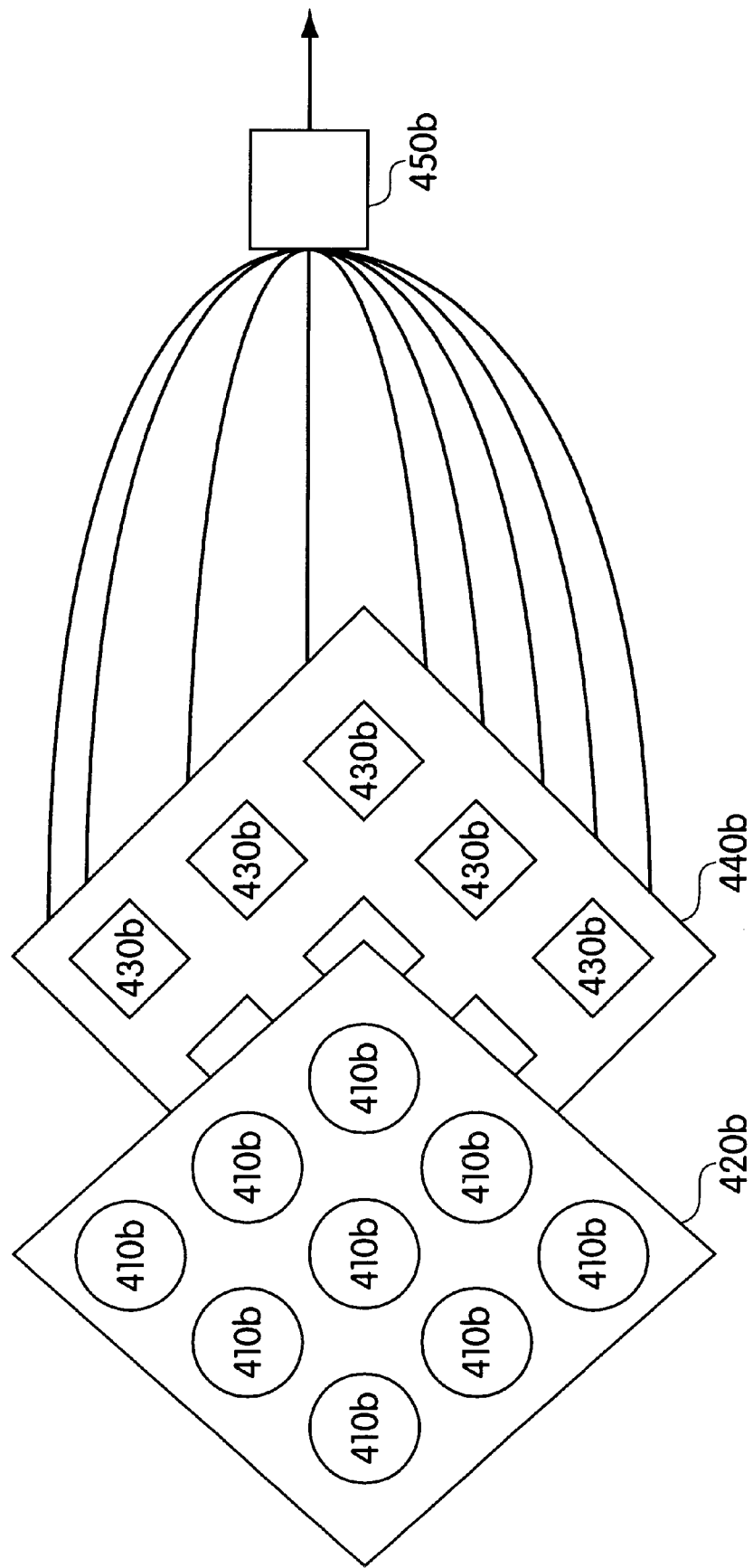
FIG. 4B is a diagram of an exemplary photodetector arrangement.

Furthermore, multiple photodetectors can be arranged at a particular viewpoint to replace or correspond to different types of light sources. Referring to FIG. 4B, an exemplary photodetector arrangement is illustrated, generally corresponding to an array of lensed LEDs used in many machine vision applications. Each lens 410B of a lenslet array 420B focusses light onto a corresponding photodiode 430B of a photodiode array 440B. The output signal from each photodiode 430B is applied to a summing amplifier 450B. The output signal from the summing amplifier 450B may then be sampled. In another embodiment, the output signal from each individual photodiode 450B may be individually sampled. The arrangement of FIG. 4B is particularly suitable for viewing certain specular surfaces which are normally best viewed with distributed light sources. As an alternative, a single fiber bundle or light guide may be used to gather the light from each lenslet at its focal point and the light from all of the bundles or light guides may be summed at a single photodetector.

In applying the principles of the present invention, a major benefit is that commercially available machine vision system optics or fiber optics may be utilized. For example, Fiber-Lite®, manufactured by Dolan-Jenner Industries, is an illumination system that couples a light input through a fiber optic assembly to form a line of light (MV-IND150LA), an area of light (MV-IND150ABL), a point of light (MV-IND150FO), or a ring of light (MV-IND150RL). Any of these assemblies can be used to create a correspondingly shaped "equivalent" to the light source by replacing the light normally used as input to the fiber optic assembly with a photodetector apparatus that provides the desired output signals.

Figure 4C:
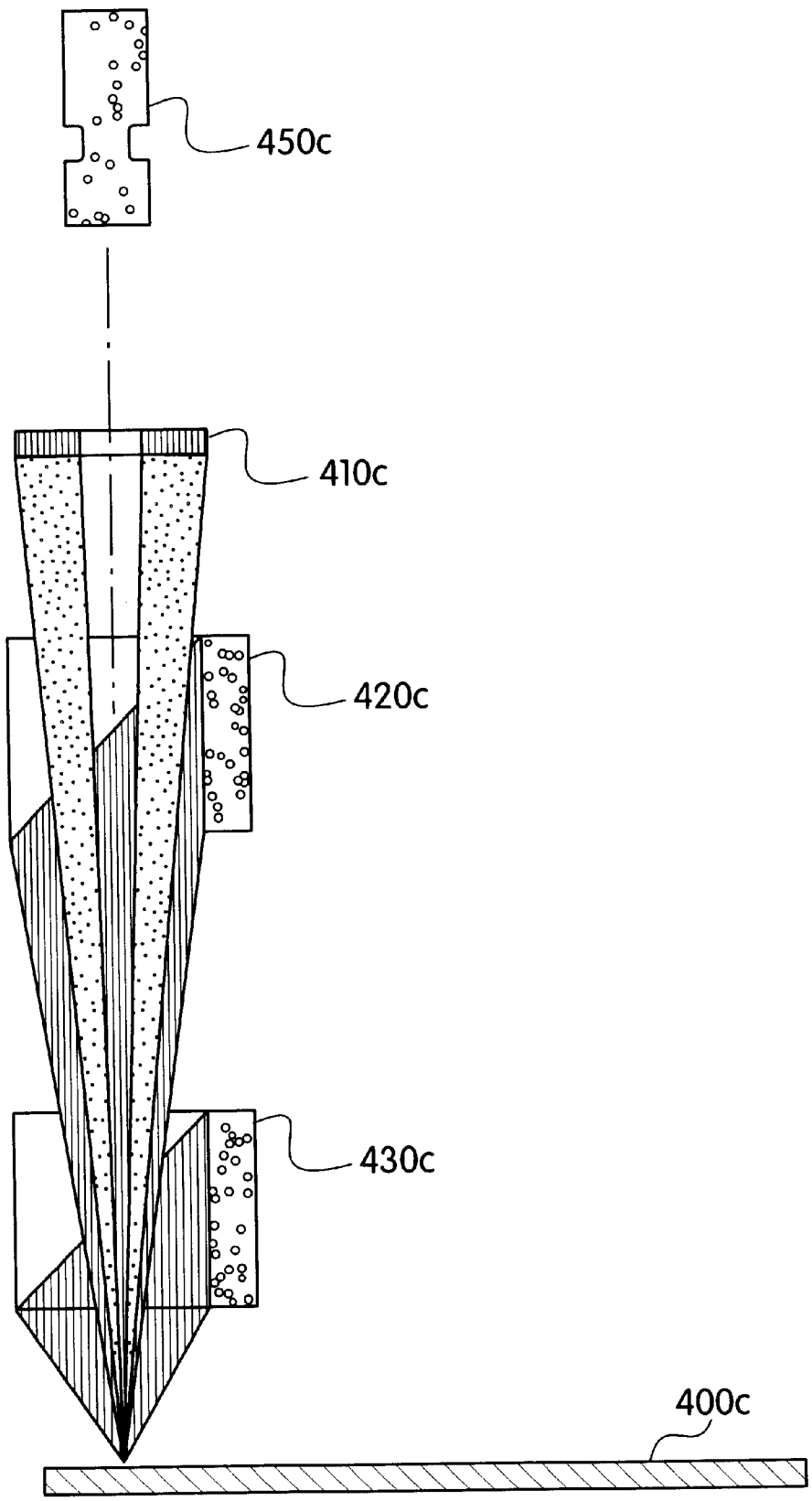
FIG. 4C is a diagram of a sequential illumination system for reading characters.

Application of the Principles of the Present Invention: When imaging characters (e.g., serial numbers) that are positioned on a semiconductor wafer, prior art systems typically require that light sources be located at a particular critical location according to the reflectance properties of both the wafer and the characters on the wafer. However, both surface and sub-surface properties may change depending on where in the semiconductor manufacturing process (i.e., what process step) the characters are being imaged. With prior art systems, many illumination locations may have to be tested before the characters can be properly read. An example of various type of illumination that could be used for imaging characters on a wafer using standard machine vision techniques is shown in FIG. 4C. As illustrated, characters on wafer 400C are sequentially illuminated by a high dark field light source 410C, (used to produce a dark-field image), a high DOAL (diffuse on axis light) 420C (positioned to produce a bright-field image), and a low DOAL 430C (positioned to produce a bright-field image). A camera 450C must capture three separate images of the characters—one per light source.

Figure 4D:
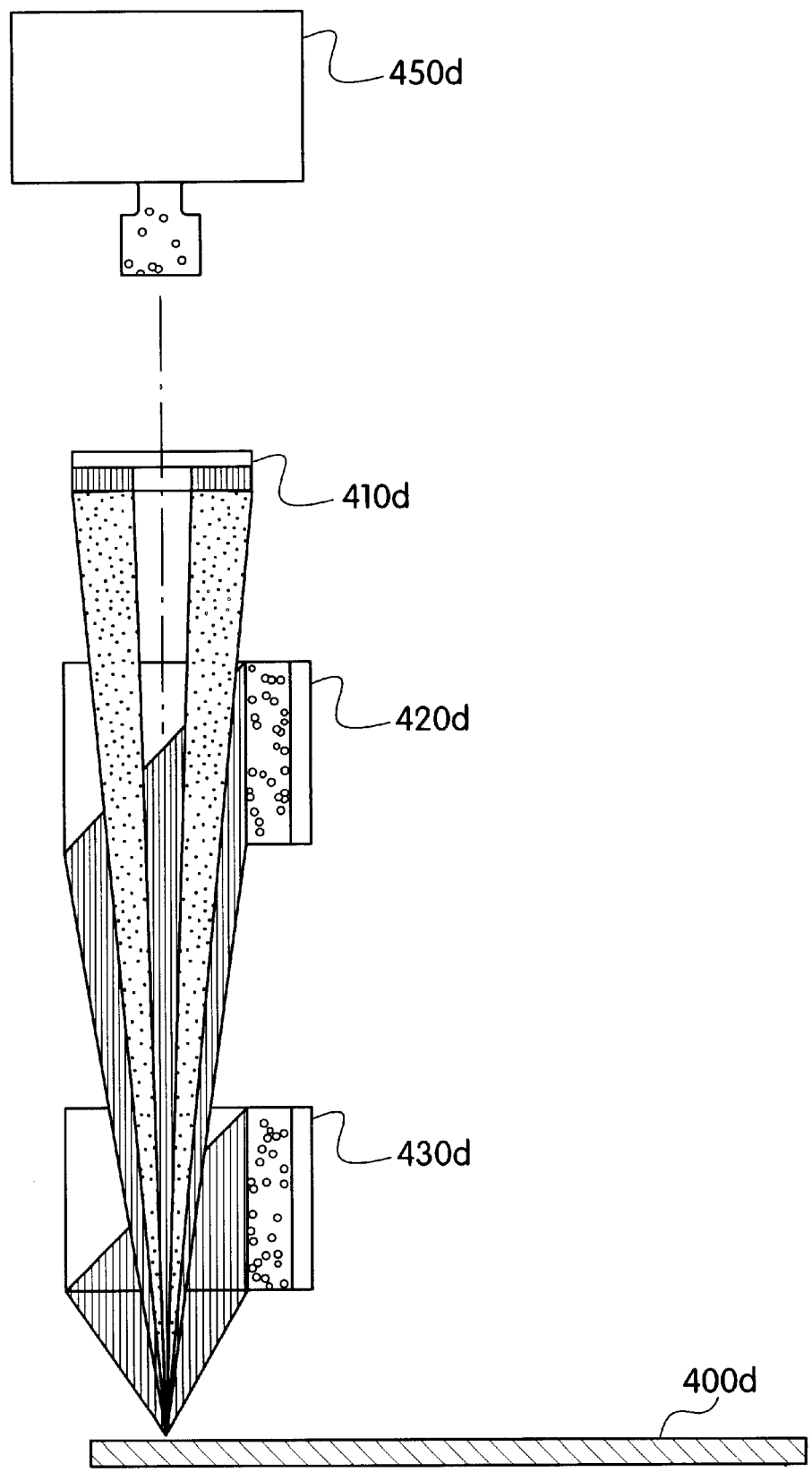
FIG. 4D is a diagram of an exemplary system in accordance with the principles of the present invention corresponding to FIG. 4C.

Referring now to FIG. 4D, in accordance with the principles of the present invention, each of the light sources (i.e., 410C, 420C, and 430C) are replaced with a corresponding photodetector (410D, 420D, and 430D) while the camera 450B is replaced with a laser scanner (450C). Here, the characters on the wafer are required to be scanned only one time, with three images being simultaneously captured by the photodetectors 410D, 420D, and 430D.

Figure 5:
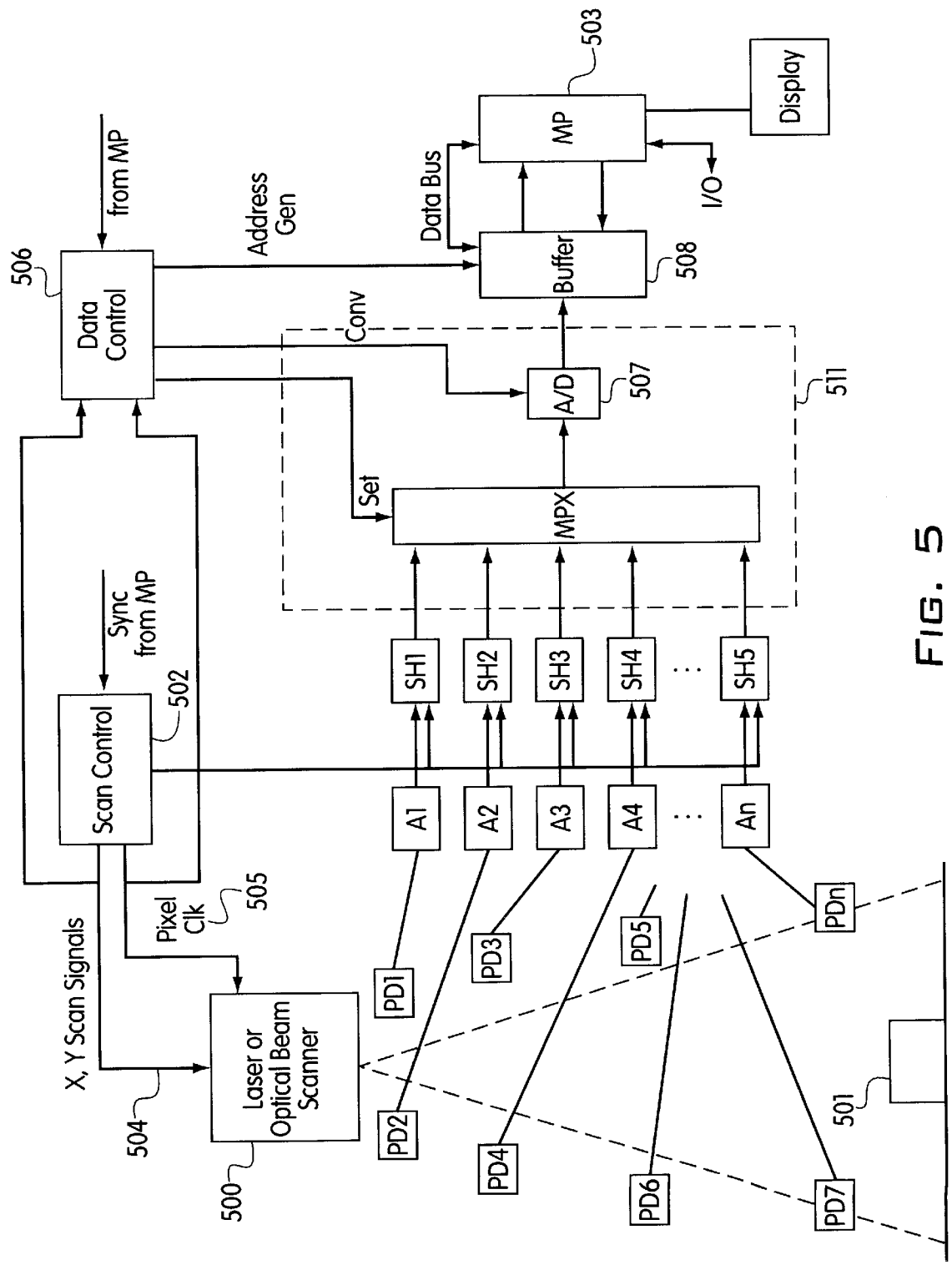
FIG. 5 illustrates the principles of the present invention in further detail.

Detailed Diagram: FIG. 5 is a diagram illustrating the general principles of the present invention in further detail. A scanner 500, positioned to illuminate an object 501 (such as, for example, a semiconductor package), is controlled by scan control circuitry 502 (under the control of sync signals from a microprocessor or associated hardware 503) to scan the object 501 in a raster pattern. Specifically, the scan control circuitry 501 provides horizontal and vertical scan control signals 504 and a pixel clock signal 505, to control the scanner 500 to sequentially illuminate each spot (i.e., pixel) on the object 501.

Photodetectors, for example, photodiodes PD1–PDn, are positioned to capture light reflected by the object 501 (as a result of illumination by the scanner 500) from various viewpoints. As illustrated, for a horizontal surface, the photodiodes positioned closest to the object 501 (i.e., photodiodes PD5–PDn) provide dark-field images while the remaining photodiodes (i.e., PD1–PD4) are positioned for bright-field imaging. However, when imaging a portion of a specular surface that is at a steep angle to the horizontal, the roles of the PD1–PD4 and PD5–PDn may reverse in which case PD5–PDn would provide bright-field images and PD1–PD4 would provide dark-field images. Depending on the complexity of the surfaces being imaged, more or less photodiodes than are shown in FIG. 5 may be used to gather sufficient data for a particular machine vision application.

Each of the photodiodes PD1–PDn is connected to an amplifier A1–An for amplifying the signals (representing the intensity of the reflected light detected by the photodiodes PD1–PDn) generated by the photodiodes PD1–PDn. Due to the variation in specularity of the surfaces of the scanned object 501, light intensity levels into the photodiodes PD1–PDn may have a very large dynamic range. Accordingly, logarithmic amplifiers may be advantageously used. In the exemplary embodiment of the present invention, although other amplifiers may be used, logarithmic amplifiers provide several advantages over linear amplifiers (although other types of amplifiers may be used):

- the logarithmic output signal is compressed so that fewer bits are needed to represent the signal—in spite of the large dynamic range;
- logarithmic output signals are easily processed when looking for significant changes (edges) since the same percentage change in a signal always corresponds to the same numeric difference regardless of the signal amplitude; and
- logarithmic output signals may be easily normalized since dividing the output signal by a reference signal is performed by simply subtracting the reference from the output.

Each of the amplifiers A1–An is connected to a sample and hold circuit (or register) SH1–SHn for sampling the signals output by the amplifiers A1–An. The sample and hold circuits SH1–SHn are synchronized with the scanner by scan control circuitry 502 so that signals representing the intensity of reflected light detected by photo detectors PD1–PDn at the same given instant in time are sampled for each spot of the object illuminated by the scanner 500. The signals output by the sample and hold circuitry SH1–SHn are applied to a multiplexer MPX. Under the control of data control circuitry 506 (which is, in turn, controlled by the microprocessor) the analog signals from the sample and hold circuitry SH1–SHn are sequentially applied to an analog to digital (A/D) converter 507 by the multiplexer MPX. The digital signals generated by the A/D converter 507 are buffered in a buffer memory 508 (or other recording device) at addresses identified by the data control circuitry 507 (under the control of the microprocessor 503).

In operation, each spot illuminated by the scanner 500 is simultaneously imaged by the photodiodes PD1–PDn. That is, for each spot illuminated at a given X-Y coordinate, a digital intensity value is stored in the buffer memory 508 representing the intensity of the light reflected by the object 501 as detected by each of the photodiodes PD1–PDn. Accordingly, for the exemplary embodiment of the present invention, n images of the object 501 are captured (i.e., one image per photodiode) as a result of a single scan of the object 501.

Figure 6:
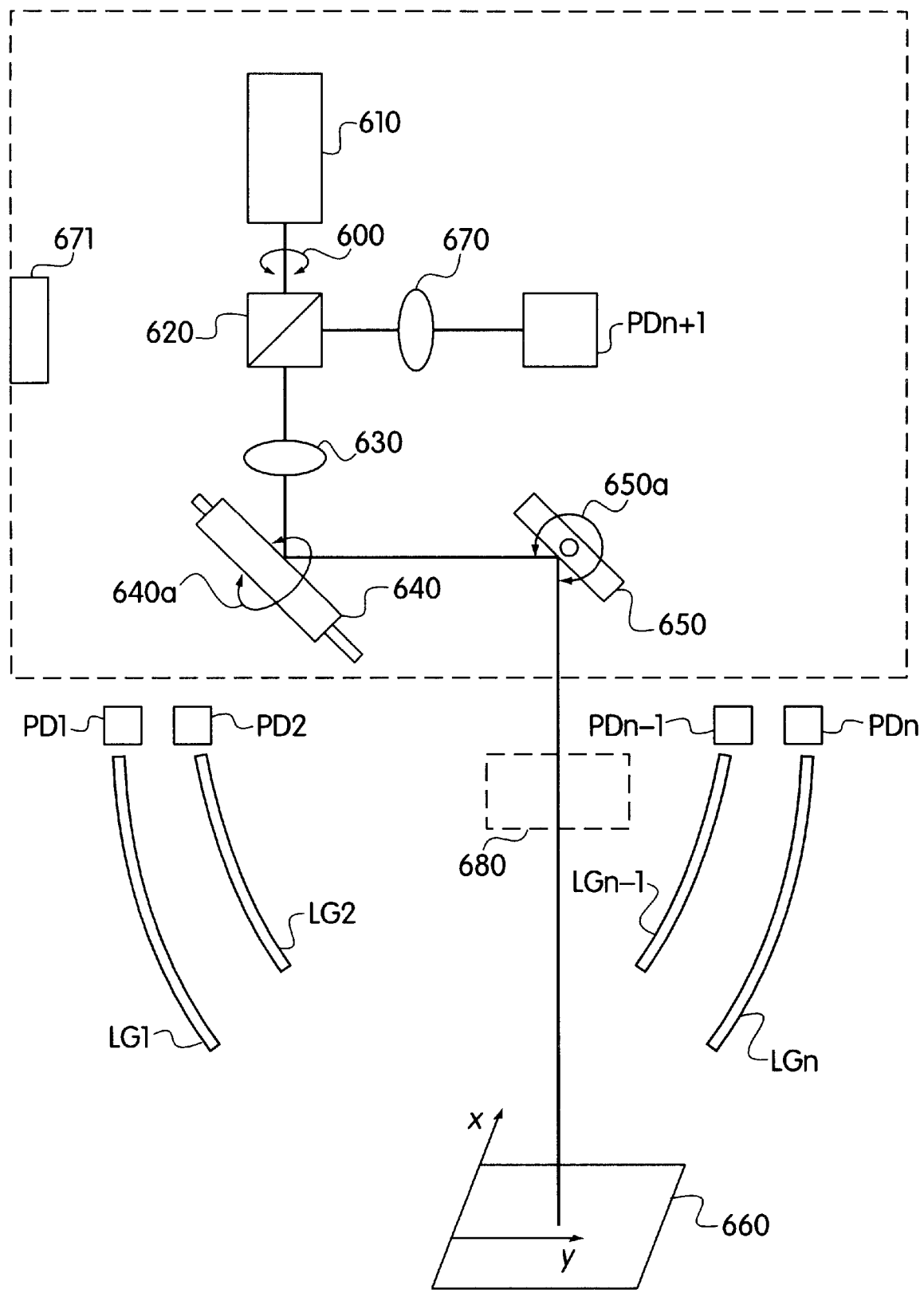
FIG. 6 illustrates the scanner and photodiode arrangement of FIG. 5 in further detail.

FIG. 6 illustrates the scanner 500 and the photodiode PD1–PDn arrangement in further detail. A light beam 600 from a light source 610, such as, for example a commercially available collimated laser diode light source, is directed though a beam splitter 620 into a lens 630 that focusses the beam 600 to a predetermined spot size on plane 660 via X and Y mirror galvanometers 640 and 650. The X galvanometer 640, controlled by the X and Y scan control signals 504 of FIG. 5 and preferably oscillating in accordance with pixel clock 505, reflects the beam 600 onto a Y mirror galvanometer 650. The Y galvanometer 650, also controlled by the X and Y scan control signals 504, reflects the beam 600 onto a point of the object 660 under examination. As will be understood by those of skill in the art, sequentially moving the X galvanometer 640 in the direction of arrow 640A causes the beam 600 to illuminate points on the object's surface along an X axis, while sequentially moving the Y galvanometer 650 in the direction of arrow 650A causes the beam 600 to illuminate points along a Y axis. Accordingly, the scanner 500 is controllable to illuminate each point on the object's surface 660 in a raster pattern. This spot may be illuminated continuously or just during a brief interval at each pixel position as it travels from one pixel position to another according to the pixel clock signal 505.

In another embodiment, the X galvanometer 640 may be replaced with a fixed mirror so that the object 660 is scanned in a single line along the Y axis. The object 660 may then be translated in the X direction via a conveyor or translation table in order to raster scan the object 660. Similarly, the Y galvanometer 650 may be replaced with a fixed mirror and the object 660 translated in the Y direction, or both galvanometers 640 and 650 may be replaced with fixed mirrors and the object translated by an X-Y translation table.

Furthermore, although galvanometers 650 and 660 are shown, other deflection devices such as rotating polygons with mirrored surfaces, rotating prisms, and acousto-optic beam deflectors, all of which are well known in the art, may be used to obtain the desired scan pattern. Also, the light beam deflection optics may have many variants such as the use of potical scan lenses 680 (for example, an F-Theta or telecentric lens) between the last beam deflector (here, galvanometer 650) and the object which can be used to provide a more uniform scan pattern or a pattern in which the beam remains substantially perpendicular to surface 660 over all X,Y beam positions.

As shown in FIG. 6, the scanner 500 of the exemplary embodiment further includes a lens 670 which focusses light reflected from the object along the beam path 600 onto a photodiode PDn+1 to sample the light that returns directly along the illumination path. This photodiode corresponds to light source 170 of FIG. 1A. Also, a stop 671 is included to absorb light that is deflected by beam splitter 620.

In the exemplary embodiment of the present invention, light guides LG1–LGn are distributed around the periphery of an imaginary hemisphere surrounding the object such that their respective input ends are uniformly angularly spaced when viewed from the center of the hemisphere (i.e., the approximate object location). Simple patterns such as closely packed circles or hexagons may be used to evenly space the input ends of the light guides LG1–LGn in azimuth and elevation along the entire surface of the hemisphere, each of the ends in a center of a circle or hexagon. In the exemplary embodiment, if hexagons are used, the axis of the center beam from scanner 500 may be aligned with a corner where three hexagons meet. Alternatively, the axis of the center ray beam of the scanner 500 may be aligned with the center of the "top" hexagon. Many other distribution schemes are possible.

In the exemplary embodiment, each of the individual light guide LG1–LGn input ends may lie above or below the surface of the hemisphere. However, each light guide LG1–LGn input end is positioned to maintain the desired angular location when viewed from the object. Output variations between the photodetectors that are connected to light guides LG1–LGn whose input ends are closer or further to the object may be removed during equipment calibration or via computation. Computations are based on the known distance between each input end and the normal object location using the inverse square law.

The output ends of the light guides LG1–LGn are proximity focused onto associated photodetectors, i.e., photodiodes PD1–PDn (described above in connection with FIG. 5).

In an alternative embodiment, a separate lens may be used to image the output end of each light guide LG1–LGn onto its corresponding photodiode PD1–PDn.

Also, a separate lens may be used to image the field of view onto each light guide input end. When such is the case, the separate lens may be selected with a large numerical aperture for maximum light capture. Depth of field and exact focus are not as important considerations as they would be in a camera lens which must resolve adjacent pixels. If the lens associated with the input end of the fiber is somewhat out of focus so that light spills outside of the fiber end, it merely reduces the amount of light captured—it down not affect the sharpness of the captured image. Conversely, depth of field and focus is an important issue for the raster scanned beam. If this beam is out of exact focus or if the scene being scanned does not fall into the depth of field of the scanning beam, the captured image will be blurred since the light spot impinging on the surface being scanned may be significantly larger than the space between pixels as defined by the distance between illuminating pulses or recording intervals. Maximizing the depth of field requires minimizing the numerical aperture of the spot scanner optics, which makes it important to choose a bright source if it is desired to maintain a high level of illumination. When the brightest spot is desired, a laser is a suitable light source. When using a laser for illumination, it is also possible to use narrow bandpass light filters (for example, of 10 nm width) to eliminate ambient light while passing scanned light reflected from the scene into the phtodetectors. Such filters may be placed anywhere in the light path between the scene and the photodetectors.

In accordance with the exemplary embodiment, when substituting photodetectors for a light source at a particular viewpoint as described in connection with FIGS. 4A, 5, and 6, several factors may be taken into account, such as, for example, sensitivity at chosen wavelengths, dynamic range, and frequency response. Avalanche photodiodes are generally very fast devices with large dynamic ranges and are particularly well suited for capturing high speed pulses at extremely low light levels due to their very high sensitivity. Photomultipliers have similar properties.

The ordinary photodiode, p-i-n photodiode, or phototransistor is also capable of good performance in video application but is of less utility with extremely high speed pulses at extremely low light levels. All of the solid state photodetector devices lose their high frequency capability as their area (and hence capacitance) increases. Accordingly, although it would appear easiest to emulate a light source viewpoint by locating the photosensitive device at the desired position and enlarging its area until it equaled that of the light source it was replacing, the loss of high frequency response and increase in attendant noise (due to increased area) will not always permit this approach.

One exemplary approach, however, is to use a lens to image the scanned scene onto the photosensitive device. This increases the energy collected to that collected over the area of the lens without increasing the area of the photodetector (with all of the corresponding disadvantages). Alternatively, in some applications, a non-imaging device, such as, for example, a tapered light pipe, may be used instead of a lens. With certain limits, the gain achieved via a tapered light pipe is equal to the input area divided by the area exiting to the photodetector. If an attempt is made to achieve too high a gain, the output rays will emerge almost parallel to the photodetector surface, and by Fresnel relationships, be reflected by the photodetector rather than absorbed.

Calibration: The exemplary embodiment illustrated in FIGS. 5 and 6 may be calibrated by scanning a flat white object and normalizing the output from each photodiode PD1–PDn with respect to each other. The correction values for normalization may then be stored in a table in memory accessible by microprocessor 503, and used during image processing. Although one value could be recorded for each illuminated position of the raster scan, it may only be necessary to store a small subset of this information since the correction values will generally vary very slowly across the field of view.

Figure 7A:
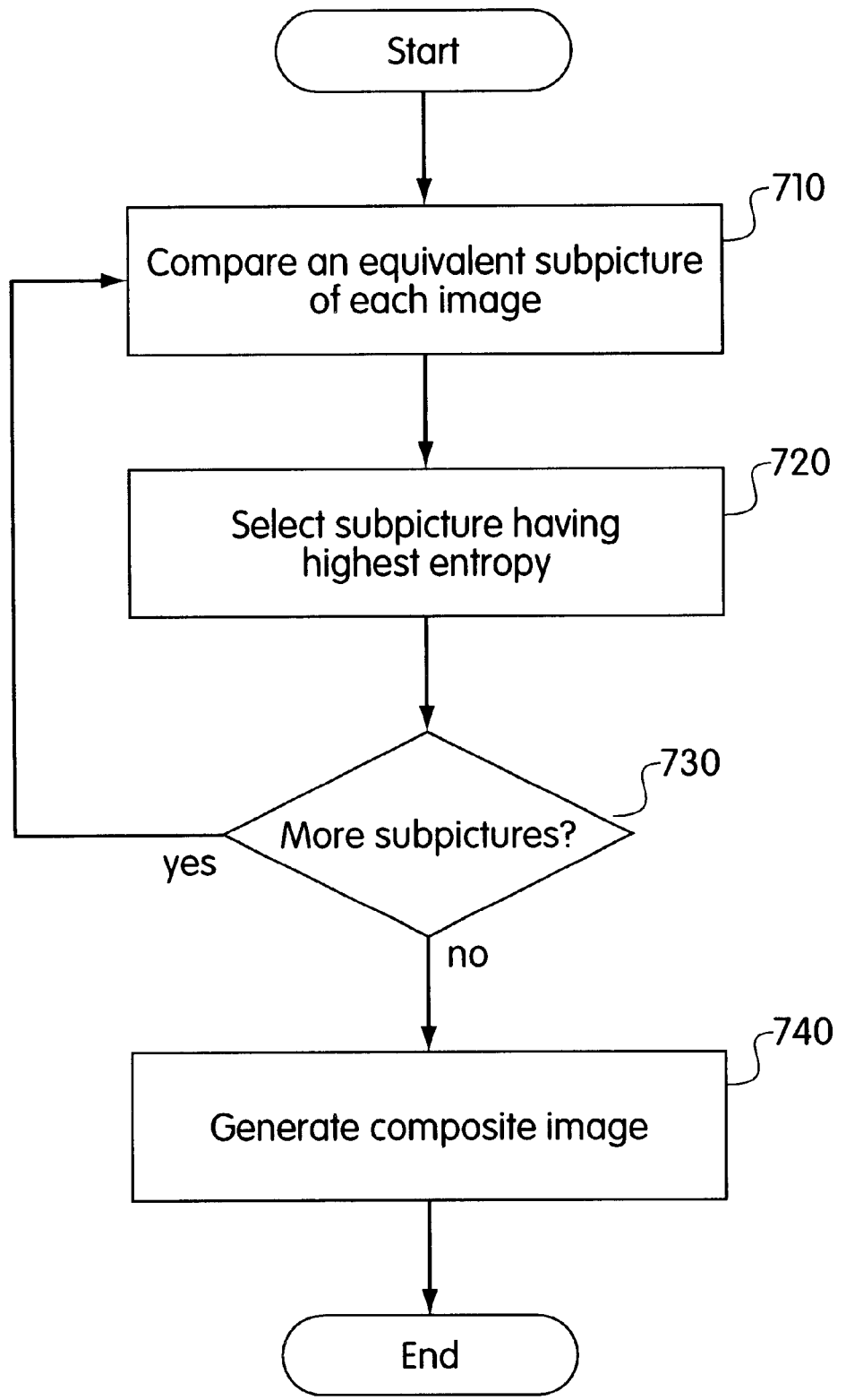
FIG. 7A is a flowchart of an illustrative process for patching an image.

Composite Images: When a specular object has a curved or multi-faceted surface, there may be no individual image captured that has useful data that covers the entire object. In such a case, it may be necessary for the microprocessor 503 to patch together the "best" portions (i.e., the portions having the highest information content) of each of the pictures obtained from each viewpoint to form a composite image. The flowchart of FIG. 7A shows an exemplary process performed by the microprocessor 503 for "patching" an image.

In accordance with the exemplary process, equivalent regions of each image (corresponding to geographically identical subpictures) are compared(step 710). Since the "useful" portion of a scene will generally be the portion with the highest entropy—in a practical sense, the portion with the most change or "detail," the subpicture having the highest entropy (for the image information sought) is selected and is stored in memory (step 720).

One way to determine the entropy of each subpicture is to pass each subpicture through a 2-D high-pass spatial frequency filter and then square each resulting pixel value. If desired, each pixel may be compared to a threshold value and set to zero if less than the threshold value (in order to eliminate pixels representing noise). The pixel values in the subpicture may then be summed to obtain a value for the entropy of the subpicture.

When certain characteristics of the subpicture desired are known in advance, such as the particular frequency or pitch that may be present in the image of a 2-D bar code, the subpicture may be passed through a corresponding bandpass spatial filter in place of, or in addition to, the aforementioned high-pass filter.

This process of FIG. 7A continues until all subpictures have been considered (step 730). A new composite picture is then generated (by patching together the selected subpictures) (step 740) that best expresses the detail or structure of the pattern or object being examined.

In the exemplary embodiment, patching is simple because there is no perspective distortion due to the varied viewpoints. Data captured at the same instant of time at each viewpoint will almost always be from the same illuminated spot or "pixel." Occasionally light may be received via a multiple reflection, but this will not be the usual case.

As one of skill in the art will understand, however, it may be necessary to conform the selected subpictures to each other. For example, assume that images are represented by N×M bit matrices wherein a "1" represents bright and a "0" represents dark. If a bright field subpicture and a dark-field subpicture are to be patched together, each bit in one of the subpictures, for example, the dark-field subpicture, is XOR'ed with a "1" so as to "flip the bits" of the subpicture to conform it to the bright-field subpicture. In effect, the dark-field subpicture is converted to an equivalent bright-field subpicture. Of course, the bright-field subpicture may be converted to an equivalent dark-field subpicture in a similar manner.

Although the composite image obtained as described in connection with FIG. 7A may be processed to reveal edges, a composite edge image or composite gradient magnitude image may also be derived directly from the individual images obtained from each of the photodetectors.

Figure 7B:
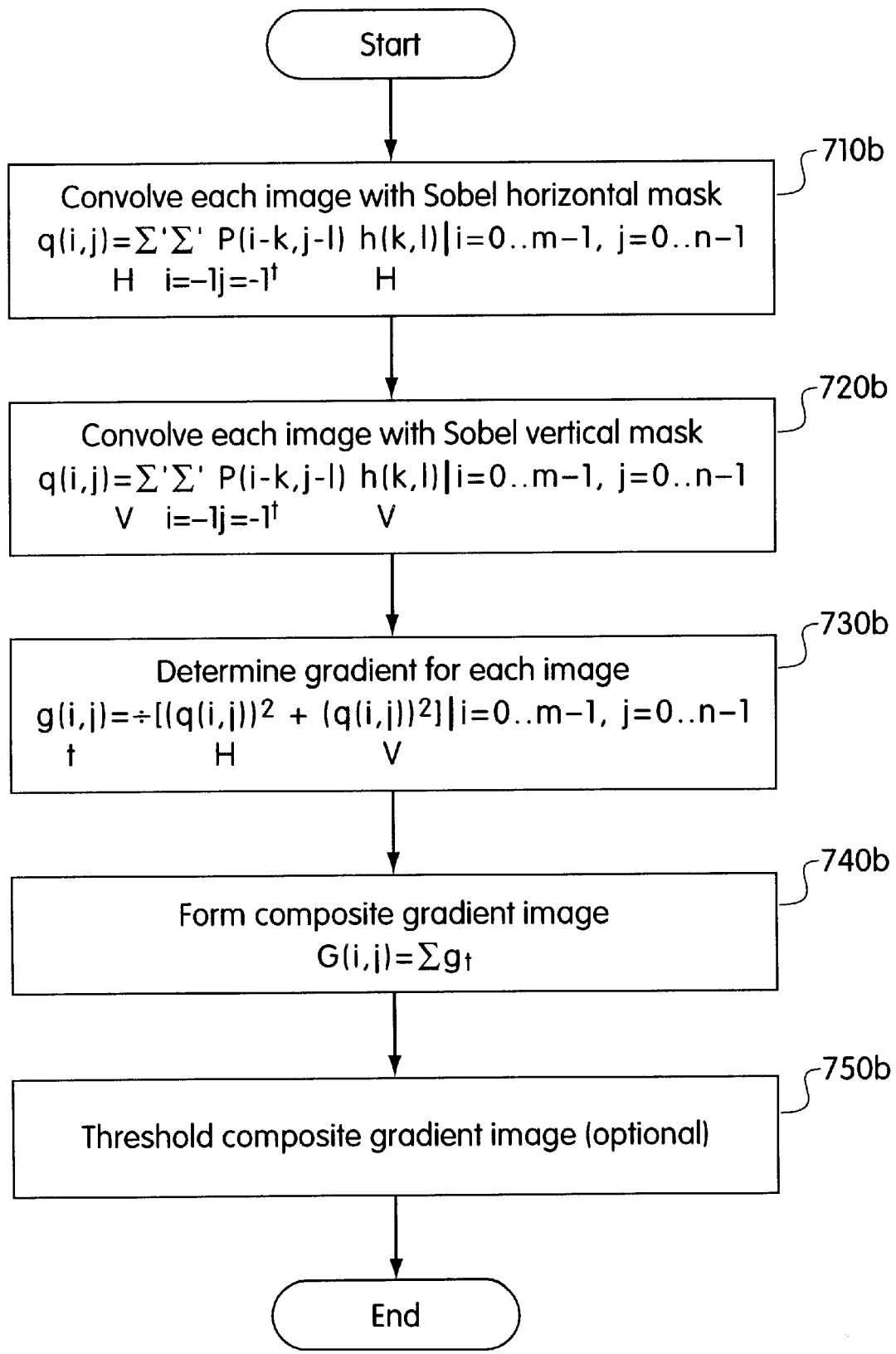
FIG. 7B is a flowchart illustrating composite gradiant image generation.

FIG. 7B is a flowchart of an exemplary process for deriving the composite gradient magnitude image directly from the individual images. Gradient magnitude is computed as follows:

$$df/dr = \sqrt{[(df/dx)^2 + (df/dy)^2]} \quad | \quad i = 0 \ldots m-1, \ j = 0 \ldots n-1$$

Accordingly, in step 710B, df/dx is derived (for each of the image matrices $P_1$–$P_s$ obtained from the photodetectors) from the convolution of each image matrix $P_1$–$P_s$ with the Sobel horizontal mask $h_H$ (i.e., the Sobel kernal sensitive to vertical edges):

$$h_H = \begin{bmatrix} 1 & 0 & -1 \\ 2 & 0 & -2 \\ 1 & 0 & -1 \end{bmatrix}.$$

Thus, $$q_h(i,j) = \sum_{i=-1}^{1} \sum_{j=-1}^{1} P_t(i-k, j-l)h_H(k,l) \ | \ i = 0 \ldots m-1, \ j = 0 \ldots n-1$$

is calculated for each image matrix (step 710B).

Next, in step 720B, df/dy is derived for each of the image matrices P from the convolution of each image matrix $P_1$–$P_s$ with the Sobel vertical mask $h_V$ (i.e., the Sobel kernal sensitive to horizontal edges):

$$h_v = \begin{bmatrix} -1 & -2 & -1 \\ 0 & 0 & 0 \\ 1 & 2 & 1 \end{bmatrix}.$$

Thus $$q_v(i,j) = \sum_{i=-1}^{1} \sum_{j=-1}^{1} P_t(i-k, j-l)h_V(k,l) \ | \ i = 0 \ldots m-1, \ j = 0 \ldots n-1$$

is calculated for each image matrix (step 720B).

The discrete gradient at image coordinate i,j is then determined for each image matrix $q_h(i,j)$ as follows:

$$g_t(i,j) = \sqrt{[(q_h(i,j))^2 + (q_v(i,j))^2]} \ | \ i = 0 \ldots m-1, \quad \text{(step 730B)}$$

$$j = 0 \ldots n-1$$

Finally, the gradient matrices $g_t(i,j)$ corresponding to image matrices $P_1$–$P_s$ are added together to provide a composite gradient magnitude image matrix G:

$$G(i,j) = \Sigma g_t \text{ (step 740B)}.$$

The composite gradient image may be optionally thresholded (step 750B).

Reflectance: The vector of relative light values gathered for each pixel or region being illuminated (i.e., one value for each photodiode PD1–PDn of FIG. 5) provides a means to infer reflectance properties (e.g., the surface is specular or matte) of points or regions illuminated on the object or pattern.

For each vector of relative light values collected for each pixel, for example, the following may be determined by the processor 503 or external circuitry (not shown):

1) the location of the photodetector that has the largest signal and its signal amplitude (the signal amplitude may be used as a reference and the location used to determine the orientation of the point corresponding to the pixel on the object surface);
2) the total (relative) energy received (calculated by, for example, adding together the intensity values represented by each of the signals generated by the photodetectors as a result of detecting light);
3) the median signal amplitude as a fraction of the reference;
4) the mean signal amplitude as a fraction of the reference;
5) the distance from the reference sensor (for a given configuration, the location of each of the sensors is known thus the distance is easily calculated) that must be traveled to obtain a significant fraction of the total energy received (e.g, the fraction of the total number of detectors that capture almost all of the energy)—(this may be calculated, for example, by adding the largest signals—in size order, largest first—until the total is a predetermined percentage of the total energy received by the system and determining how many of signals were added);
6) the standard deviation of the energy received; and
7) the ratio of the largest element of the vector (i.e., the highest light intensity value) to the smallest.

Figure 8:
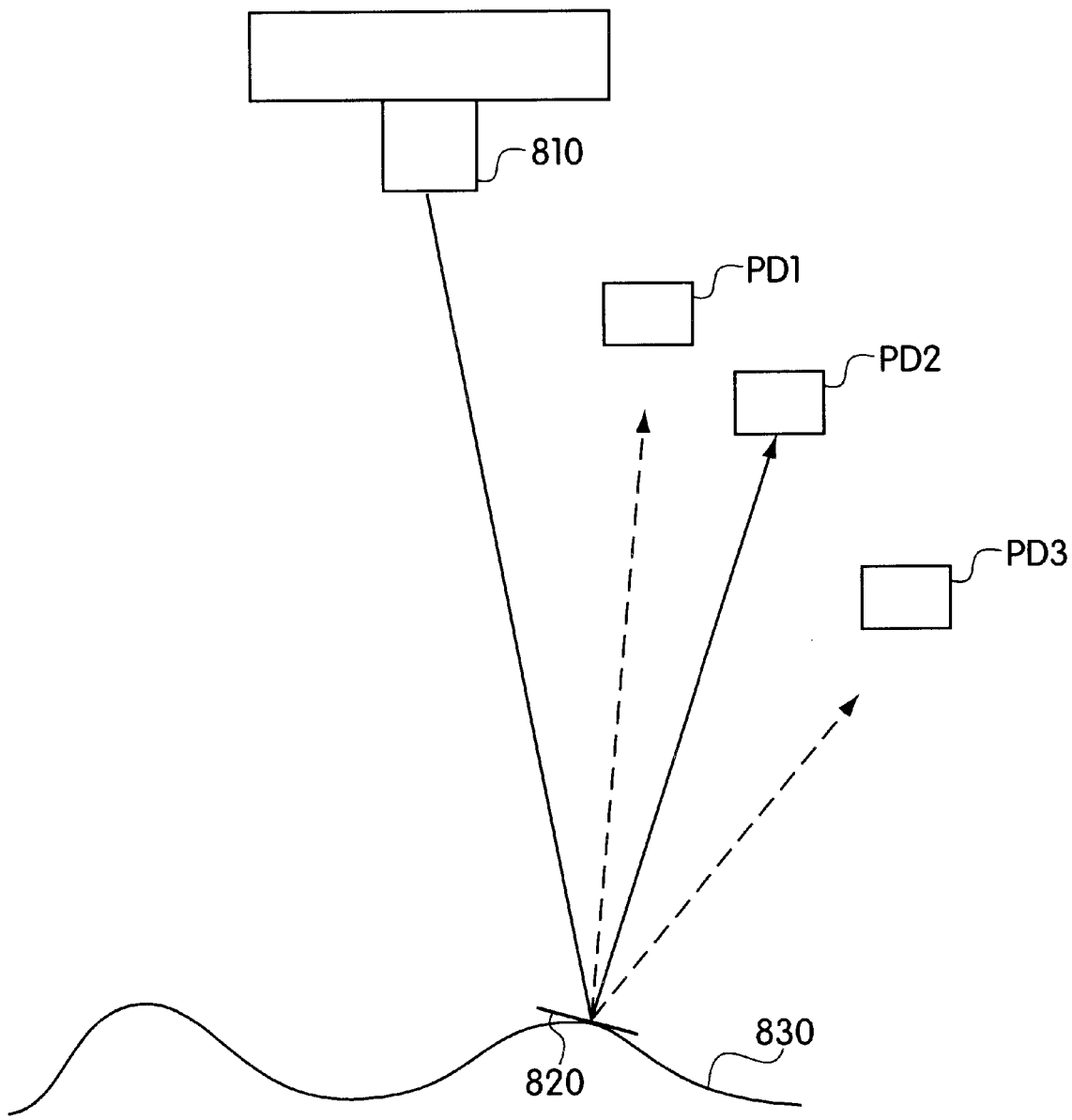
FIG. 8 illustrates a scanner illuminating a point on a surface.

From the above-listed calculations, reflectance properties may be inferred. If, for example, a point on an object is highly specular (in an ideal sense), one photodetector would receive all (or most) of the reflected light energy. As shown in FIG. 8, for example, a scanner 810 illuminates a point 820 on a surface of an object 830. If the object is specular at the point 820, the reflected light intensity detected by one of the photodiodes (in this case, photodiode PD2) will likely be significantly larger than the light detected by neighboring photodiodes (here, photodiodes PD1 and PD3). Similarly, if the vector of light intensity values associated with illumination of the point 820 consists of approximately equal values (except for the cosine falloff with angle), the surface being illuminated is diffuse or matte.

Accordingly, reflectance properties would be evident from all of the values calculated in connection with 1) through 7) above. However, not all values are necessary to infer reflectance properties. For example, the value calculated for item 5, i.e., the fraction of the total number of detectors that capture almost all of the energy, may be sufficient to infer specularity (e.g., item 5 would be very small). Similarly, if the point is completely matte, the computed values corresponding to items 1, 3, and 4 will be close in amplitude. Moreover, the computed values corresponding to items 6 and 7 will be small.

Because reflectance properties corresponding to a point are contained in the computed relationships of the values in the vector (as set forth, for example, in items 1–7 above), the amount of information that must be stored and processed to sufficiently describe these properties can be significantly decreased. Rather than storing each element of the vector (each element corresponding to one photodetector), it may be only necessary to store a subset of values corresponding to the computed properties of the vector. For example, under certain circumstances, recording items 1, 5, and 6 (above) for each point scanned (as derived from the vector of light intensity values associated with that point) provides sufficient information to infer reflectance. This may be done on a pixel by pixel basis.

In some other circumstances it may only be necessary to store a single bit, a "1" for specular and a "0" for non specular, etc., for each input vector, according to a decision made based on vector data. The data required to be kept will be application specific.

Pre-Processing Circuitry: When a reduction in the amount of data recorded as described above is desired, the input vector must be examined or pre-processed between illumination of adjacent pixels. Accordingly, special purpose hardware can be used to ensure that the required processing can be done in the inter-pixel time interval. Such special purpose processing may take advantage of parallel architecture or mixed analog and digital processing to obtain the necessary speed. The portion of the system outlined in dashed lines 511 illustrated in FIG. 5 may be replaced with such pre-processing hardware.

Figure 11:
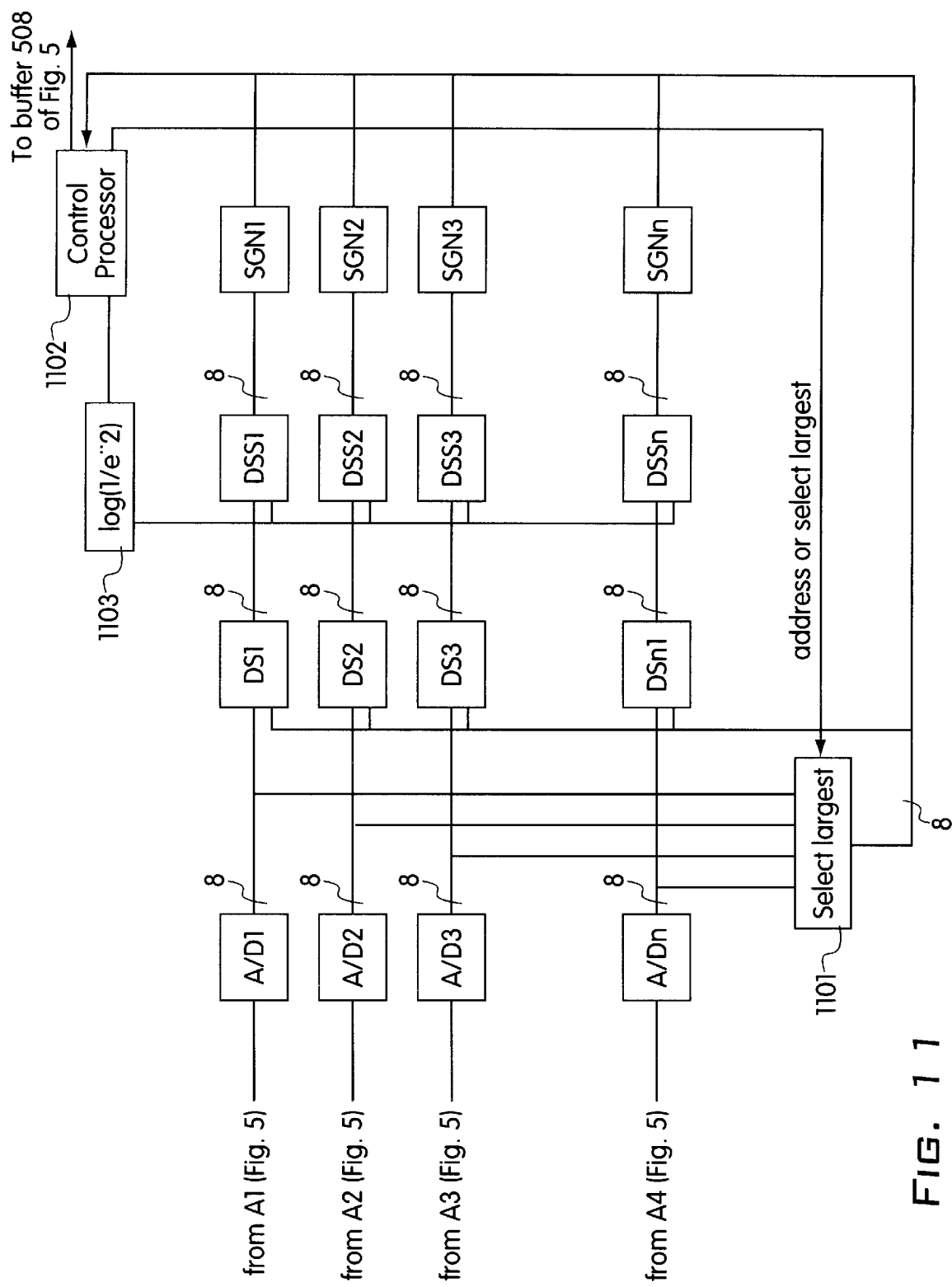
FIG. 11 is a diagram of an exemplary embodiment of pre-processing hardware.

FIG. 11 illustrates an exemplary embodiment of the pre-processing hardware. As illustrated, the signals from each of the log amplifiers A1–An of FIG. 5 are applied to corresponding analog to digital (A/D) converters A/D1–A/Dn where the analog signals are converted to eight bit digital signals. The digital signals from the A/D converters A/D1–A/Dn (each digital signal representing one vector element) are applied, in parallel to that logic circuit 1101 which identifies and extracts the largest digital signal.

The details of logic circuit 1101 are not shown since there are any number of ways that this can be designed. For example, the most significant bit of each vector element may be examined. Elements having a "0" in this position may be eliminated from further consideration if any of the other elements have a "1" in the same position. This may be repeated for each bit position, one at a time, until the least significant bit of the elements have been considered. At that time, only the largest of the elements will remain. Although this can be performed as a sequential process, it may be advantageous to implement this operation (circuit 1101) as a parallel process by using hard wired logic (using, for example, a PAL, an ASIC, etc.) to obtain high speed operation. Using additional gating at the logic circuit 1101, a processor 1102 may address any of the vector elements in order to use the logic circuit 1101 as a demultiplexer or selector switch.

The element extracted as the "largest" (i.e., a "reference" value) can now be used to normalize the other vector elements. Since the vector elements are log functions (as when amplifiers A1–An are log amplifiers), normalization can be accomplished using digital subtraction circuits DS1–DSn. Specifically, the digital signals from A/D converters A/D1–A/Dn are applied to the positive input of corresponding subtraction circuits DS1–DSn where the "largest" vector element from logic circuit 1101 is subtracted from each. The result will be a negative number for each of the elements (except, of course, for each element equal to the "largest" vector element) that is proportional to the log of the ratio of each element to the reference value.

Next, the processor 1102 polls the element values to rapidly determine which element values are larger than some particular fraction of the energy of the reference value. For example, if the processor is to determine the number of elements whose power is at least $1/e^{}2$ of the reference value, each of the signals output from the digital subtractors DS1–DSn are applied to the positive input of corresponding digital subtraction circuits DSS1–DSSn, and $\log(1/e^{}2)$ 1103 is subtracted therefrom. The elements that have more power than $1/e^{**}2$ of the reference value produces a positive value at the output of corresponding subtraction circuits DSS1–DSSn. The elements that have less power produce a negative value at the output of corresponding subtraction circuits DSS1–DSSn.

The signals from the digital subtraction circuits DSS1–DSSn are applied to corresponding sign function (sgn) circuits SGN1–SGNn, each of which output a high or positive signal if the input signal is positive and output a low or negative signal if the input signal is negative. The signals output by the sgn circuits SGN1–SGNn are transmitted to the processor 1102. A processor (i.e., processor 1102) having an n bit word can thus identify which of the n element values exceed a particular fraction of the reference power.

With the hardware described above, it is possible to obtain a new vector containing far fewer data bits than the number of bits in the original vector, and yet still have sufficient information to enhance the image processing or other machine vision operation via knowledge of the reflectance properties of the individual pixels.

Figure 12:
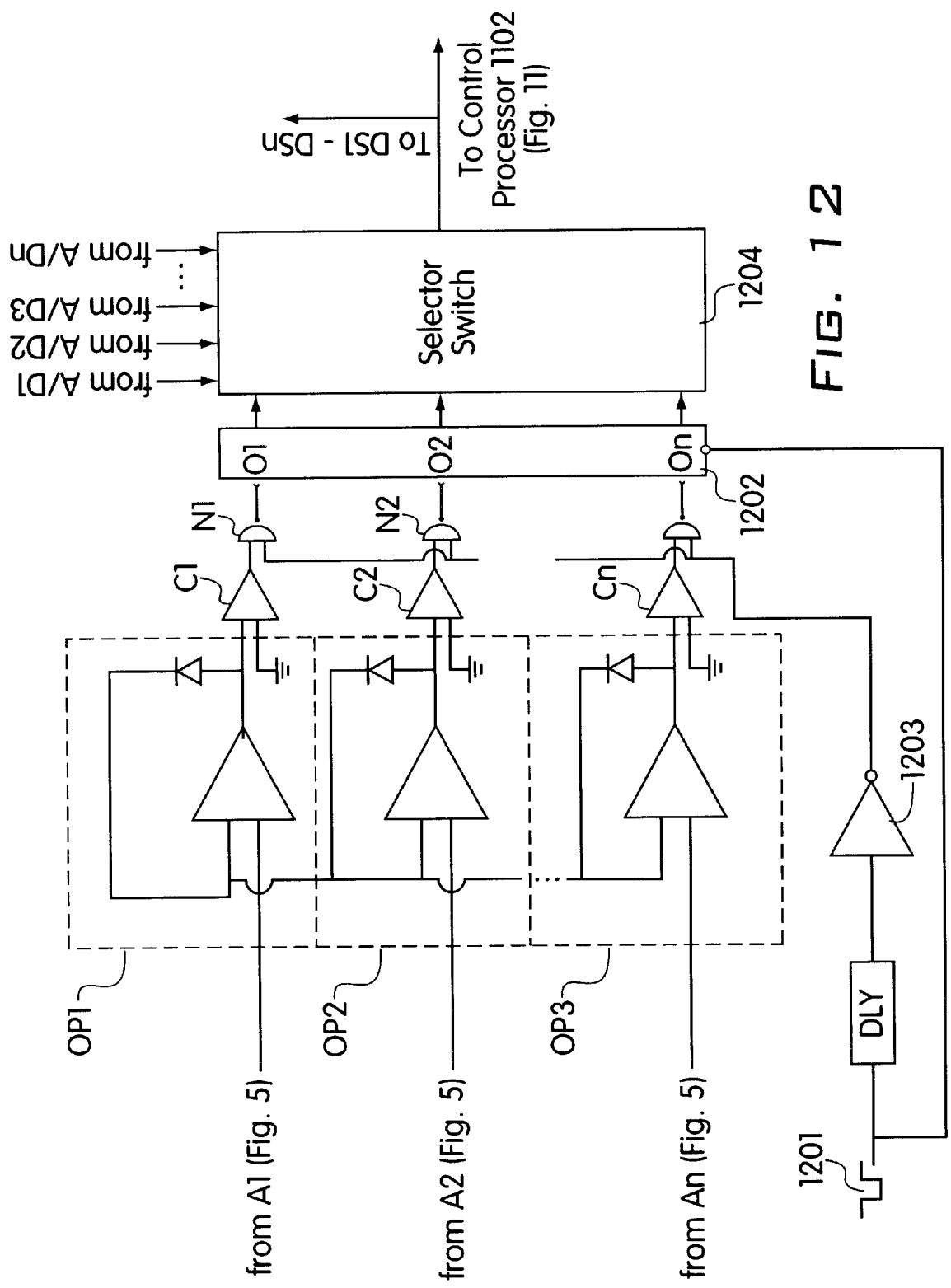
FIG. 12 is a diagram of an enhancement to FIG. 11.

The diagram of FIG. 12 illustrates an enhancement to the pre-processing circuitry of FIG. 11. In particular, the logic circuitry illustrated in FIG. 12 replaces logic circuit 1101. As illustrated, the analog signals from amplifiers A1–An of FIG. 5 are applied to corresponding high speed operational amplifier ("op amp") with diode networks OP1–OPn. The op amp network(s) OP1–OPn corresponding to the largest signal(s) input from amplifiers A1–An generate a positive output signal. The remaining networks OP1–OPn generate a negative output signal.

The signals from networks OP1–OPn are applied to corresponding comparators C1–Cn which convert the positive signals to "1's" and negative signals to "0's." These signals are then each applied to a first terminal of corresponding NAND sample gates N1–Nn.

A negative pulse 1201 resets latches 1202 before each illumination light pulse. This pulse is also inverted by invertor 1203 (after a delay) and applied to each of the second terminals of NAND gates N1–Nn. The signals output by each NAND gate N1–Nn are applied, in parallel, to latches 1202 which latches the applied signals. The signals from latches 1202 are then applied to a selector switch 1204 to select the appropriate signal (i.e., the largest signal) from the signals received from A/D1–A/Dn. The selected signal is then output at output terminal 1205 and may then be used as the reference signal (described above in connection with FIG. 11).

2-D Bar Code: Determining the reflectance property of each point on a surface is particularly useful in a machine vision application such as reading two-dimensional ("2-D") Bar Codes and data matrix symbols (as described in U.S. Pat. Nos. 4,939,354 and 5,053,609, both expressly incorporated herein by reference). Bar Codes and data matrix symbols are typically generated on a part by altering its local reflectance properties via laser marking, sandblasting, peening, or other means. In the exemplary embodiment, the processor 503 analyzes the information stored regarding each point (e.g., items 1, 5, and 6 above) and generates a two dimensional bit matrix representing the inferred reflectance property of each point illuminated on the object's surface. FIG. 9 illustrates a portion of the generated matrix 910 representing a data matrix symbol sandblasted on a specular surface (such as, for example, stainless steel). Here, a "1" identifies that the corresponding point on the object's surface is highly reflective or specular while a "0" identifies that the point is matte. By analyzing this matrix 910, the processor can easily decode the two dimensional data matrix symbol.

Surface Orientation: The vector of relative light values gathered for each pixel also provide a means to infer the surface orientation of points or regions illuminated on the object or pattern. As illustrated in FIG. 8, the normal to the surface at that location may be determined by observing which photodiode detected the highest intensity reflected light, since at approximate locations of the light source 810, the photodiodes PD1–PD3, and the object 830 are known.

2-D And 3-D Images: As a person of skill in the art will understand, the present invention can be applied to simultaneously obtaining multiple 2-D images of an object, simultaneously obtaining multiple three-dimensional (3-D) images of an object, and simultaneously obtaining both 2-D and 3-D images of an object. One 3-D imaging technique (obtaining a single 3-D image) is described in U.S. Pat. No. 4,957,369 to Antonsson, expressly incorporated herein by reference.

Portable Scanner: It is not necessary to locate the photodetectors and the light source in the same housing, although for certain applications, a common housing may be desirable. A common housing puts all of the optical scanning and photodetection equipment into one easily handled package, and creates a known fixed geometric relationship between the light source and the various photodetectors. This fixed relationship is useful for computing ranges via triangulation and for taking distance and angle into account when determining reflectance properties. The photodetectors may be multi output position sensing devices where a ratio of signals indicates angle and the sum of the signals indicates the light values, as disclosed in U.S. Pat. No. 4,957,369 issued to Antonsson, expressly incorporated herein by reference. However, for portable hand held applications, it may be advantageous to physically separate the functions so that the laser scanning function can be operator held and made as small and lightweight as possible. The photodetectors and processing equipment may be distributed throughout the room or work area where the hand held scanner will be used. Most of the photodetectors, however, should not be shadowed from the area of the object that is being scanned by the light spot.

The object can be located at a large distance from the hand-held laser scanner as long as the laser spot is kept reasonably well focussed on the object surface. There are many ways that focus can be maintained. The simplest are based on normal camera-based autofocus techniques such as sonic ranging, maximizing detail, meter ranging, etc. These known systems can be built into the hand held scanner. Alternatively, the scanner 500 could have its own internal light source (AC or pulsed) used as a target for two photodetectors on a known baseline. This allows the system to track the location of the hand scanner with respect to the known baseline. Since the location of the scanner location and the target location (by tracking a light spot on the object surface), the processor 503 could compute the range between the scanner and the target and use this information to adjust the optics in the scanner to maintain focus.

Other alternative embodiments: While the present invention has been particularly shown and described with reference to exemplary embodiments thereof, it will be understood by those skilled in the art that various changes in form and details may be made therein without departing from the spirit and scope of the invention.

What is claimed is:

1. A method for imaging an object comprising the steps of:

a) illuminating at least a portion of the object with light transmitted by a light source;

b) detecting light reflected from the object at a first preselected position;

c) forming a bright-field image of the illuminated portion of the object as a function of the light detected in step b);

d) simultaneously with step b), detecting light reflected from the object at a second position;

e) forming a dark-field image of the illuminated portion of the object as a function of the light detected in step d);

f) determining the entropy of a first portion of the bright-field image corresponding to a first portion of the object;

g) determining the entropy of a first portion of the dark-field image corresponding to the first portion of the object;

h) selecting either the first portion of the bright-field image or the first portion of the dark-field image as a function of the bright-field entropy and the dark-field entropy;

i) determining the entropy of a second portion of the bright-field image corresponding to a second portion of the object;

j) determining the entropy of a second portion of the dark-field image corresponding to the second portion of the object;

k) selecting either the second portion of the bright-field image or the second portion of the dark-field image as a function of the bright-field entropy and the dark-field entropy; and l) combining the selected first portion and the selected second portion to form a composite image.

2. The method of claim 1 wherein the illuminating step comprises the step of:

scanning the at least portion of the object with a collimated light source.

3. The method of claim 1 wherein the illuminating step comprises the step of:

scanning the at least portion of the object with a focused light source.

4. A method of imaging an object comprising the steps of:

a) illuminating at least a portion of the object with light transmitted by a light source;

b) detecting light reflected from the object at a first preselected position;

c) forming a first image of the illuminated portion of the object as a function of the light detected in step b);

d) simultaneously with step b), detecting light reflected from the object at a second preselected position;
e) forming a second image of the illuminated portion of the object as a function of the light detected in step d);
f) dividing the first image into a plurality of first subimages;
g) dividing the second image into a plurality of second subimages;
h) determining the entropy of one of the plurality of first subimages corresponding to a first portion of the object;
i) determining the entropy of one of the plurality of second subimages corresponding to the first portion of the object;
j) comparing the determined entropy of the one of the plurality of first subimages with the determined entropy of the one of the plurality of second subimages;
k) selecting either the one of the plurality of first subimages or one of the plurality of second subimages as a function of the result of step j);
l) determining the entropy of a second of the plurality of first subimages corresponding to a second portion of the object wherein the second portion is different than the first portion;
m) determining the entropy of a second of the plurality of second subimages corresponding to the second portion of the object;
n) comparing the determined entropy of the second of the plurality of first subimages with the determined entropy of the second of the plurality of second subimages;
o) selecting either the second of the plurality of first subimages or second of the plurality of second subimages as a function of the result of step n); and
p) combining the subimage selected in step k and the subimage selected in step o to form a composite image.

5. The method of claim 4 wherein the illuminating step comprises the step of:
scanning the at least portion of the object with a collimated light source.

6. The method of claim 4 wherein the illuminating step comprises the step of:
scanning the at least portion of the object with a focused light source.

7. A method for imaging an object comprising the steps of:
a) illuminating at least a portion of the object with light transmitted by a light source;
b) detecting light reflected from the object at a first preselected position;
c) forming a bright-field image of the illuminated portion of the object as a function of the light detected in step b);
d) simultaneously with step b), detecting light reflected from the object at a second position;
e) forming a dark-field image of the illuminated portion of the object as a function of the light detected in step d);
f) determining a first gradient image as a function of the bright-field image;
g) determining a second gradient image as a function of the dark-field image; and
h) determining a composite image as a function of the first gradient image and the second gradient image.

8. The method of claim 7 wherein the illuminating step comprises the step of:
scanning the at least portion of the object with a collimated light source.

9. The method of claim 7 wherein the illuminating step comprises the step of:
scanning the at least portion of the object with a focused light source.

10. A method of imaging an object comprising the steps of:
a) illuminating at least a portion of the object with light transmitted by a light source;
b) detecting light reflected from the object at a first preselected position;
c) forming a first image of the illuminated portion of the object as a function of the light detected in step b);
d) simultaneously with step b), detecting light reflected from the object at a second preselected position;
e) forming a second image of the illuminated portion of the object as a function of the light detected in step d);
f) determining a first gradient image as a function of the first image;
g) determining a second gradient image as a function of the second image; and
h) determining a composite image as a function of the first gradient image and the second gradient image.

11. The method of claim 10 wherein the illuminating step comprises the step of:
scanning the at least portion of the object with a collimated light source.

12. The method of claim 10 wherein the illuminating step comprises the step of:
scanning the at least portion of the object with a focused light source.

13. The method of claim 10 further wherein the determining step h) comprises:
adding the first gradient image to the second gradient image.

14. A method of imaging a semiconductor package comprising the steps of:
a) illuminating at least a portion of the semiconductor package with light transmitted by a light source;
b) detecting light reflected from the semiconductor package at a first preselected position;
c) forming a first image of the illuminated portion of the semiconductor package as a function of the light detected in step b);
d) simultaneously with step b), detecting light reflected from the semiconductor package at a second preselected position;
e) forming a second image of the illuminated portion of the semiconductor package as a function of the light detected in step d);
f) determining a first gradient image as a function of the first image;
g) determining a second gradient image as a function of the second image; and
h) determining a composite image as a function of the first gradient image and the second gradient image.

15. A method for determining reflectance properties of an object comprising the steps of:
a) illuminating a first portion of the object with light transmitted by a light source;
b) detecting light reflected from the first portion of the object at a plurality of preselected positions simultaneously;

c) generating a plurality of intensity signals corresponding to an intensity of light value detected at each of the plurality of preselected positions;

d) comparing the plurality of intensity signals; and e) determining the reflectance property of the first portion of the object as a function of a result of the comparing step, the determining step including the steps of i) identifying the first portion as diffuse if the plurality of intensity signals are substantially equal, and ii) identifying the first portion as reflective if one of the plurality of intensity signals is larger than the others of the plurality of intensity signals by a predetermined amount.

16. The method of claim 15 wherein the detecting step b) comprises the step of:

detecting light reflected from the first portion of the object at a plurality of preselected positions simultaneously, wherein the preselected positions are substantially uniformly angularly spaced with respect to the object.

17. The method of claim 15 further comprising the steps of:

f) storing a representation of the reflectance property of the illuminated portion of the object at a position in a matrix corresponding to the first portion of the object; and sequentially repeating each of steps a)–f) for a plurality of different portions of the object.

18. The method of claim 17 further comprising the step of:

using the matrix to read a Bar Code.

19. The method of claim 17 further comprising the step of:

using the matrix to read a data matrix symbol.

20. The method of claim 15 wherein the determining step d) comprises the steps of:

determining a reference intensity signal as a function of step e);

comparing the reference intensity signal to each of the plurality of intensity signals; and determining the reflectance property of the first portion.

21. A method for determining reflectance properties of an object, comprising:

a) illuminating a first portion of the object with light transmitted by a light source;

b) detecting light reflected from the first portion of the object at a plurality of preselected positions simultaneously;

c) generating a plurality of intensity signals corresponding to an intensity of light value detected at each of the plurality of preselected positions;

d) comparing the plurality of intensity signals; and e) determining the reflectance property of the first portion of the object as a function of a result of the comparing step, the determining step including the steps of i) determining a standard deviation of the plurality of intensity signals, and ii) identifying the portion of the object as matte if the standard deviation is less than a predetermined value.

22. A method for determining reflectance properties of an object, comprising:

a) illuminating a first portion of the object with light transmitted by a light source;

b) detecting light reflected from the first portion of the object at a plurality of preselected positions simultaneously;

c) generating a plurality of intensity signals corresponding to an intensity of light value detected at each of the plurality of preselected positions;

d) comparing the plurality of intensity signals; and e) determining the reflectance property of the first portion of the object as a function of a result of the comparing step, the determining step including the steps of i) adding each of the intensity values represented by each of the plurality of intensity signals to determine a total detected intensity ii) determining a number of the plurality of intensity signals that represent a predetermined fraction of the total detected intensity, and iii) identifying the portion of the object as reflective if the determined number is less than a predetermined number.

* * * * *